US008986526B2

(12) United States Patent
Collier et al.

(10) Patent No.: US 8,986,526 B2
(45) Date of Patent: Mar. 24, 2015

(54) FORMATION OF IMMOBILIZED BIOLOGICAL LAYERS FOR SENSING

(71) Applicant: Abbott Point of Care Inc., Princeton, NJ (US)

(72) Inventors: Gordon Bruce Collier, Fitzroy Harbour (CA); Jason Andrew Macleod, Ottawa (CA); Anjulia Wong, Gloucester (CA); Attila Csaba Nemeth, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 0 days.

(21) Appl. No.: 13/711,886

(22) Filed: Dec. 12, 2012

(65) Prior Publication Data

US 2013/0112558 A1     May 9, 2013

Related U.S. Application Data

(62) Division of application No. 13/478,260, filed on May 23, 2012, now Pat. No. 8,389,042, which is a division of application No. 11/961,550, filed on Dec. 20, 2007, now Pat. No. 8,241,697.

(51) Int. Cl.
*G01N 27/26*    (2006.01)
*G01N 27/40*    (2006.01)
(Continued)

(52) U.S. Cl.
CPC ... *B05C 9/12* (2013.01); *C12Q 1/00* (2013.01); *C12Q 1/26* (2013.01); *C12Q 1/28* (2013.01); *C12Q 1/42* (2013.01); *C12Q 1/58* (2013.01); *C12Q 1/006* (2013.01)
USPC ............. 204/403.1; 204/403.14; 204/403.01; 205/792; 205/778

(58) Field of Classification Search
CPC ................... C12Q 1/005; C12Q 1/58; G01N 27/327–27/3278
USPC ............. 204/403.01–403.15; 205/775, 777.5, 205/789, 792–793, 778
See application file for complete search history.

(56) References Cited

U.S. PATENT DOCUMENTS 3,962,038 A    6/1976   Kawashima et al.
4,933,048 A    6/1990   Lauks
(Continued)

FOREIGN PATENT DOCUMENTS

EP    0771867 A2    5/1997
EP    1277826 A1    1/2003
(Continued)

OTHER PUBLICATIONS

George Odian, Principles of Polymerization, Chapter 3, Fourth Edition, 2004.*
(Continued)

*Primary Examiner* — Luan Van
*Assistant Examiner* — Maris R Kessel

(57) ABSTRACT

The invention is directed to enzyme immobilization compositions comprising: one or more enzymes, a humectant, an acrylic-based monomer, a water-soluble organic photo-initiator and a water-soluble acrylic-based cross-linker in a substantially homogeneous aqueous mixture. The invention is also directed to methods for forming sensors comprising such compositions and to apparati for forming arrays of immobilized layers on an array of sensors by dispensing such compositions onto a substrate.

5 Claims, 19 Drawing Sheets

(51) Int. Cl.
*G01N 27/333* (2006.01)
*B05C 9/12* (2006.01)
*C12Q 1/00* (2006.01)
*C12Q 1/26* (2006.01)
*C12Q 1/28* (2006.01)
*C12Q 1/42* (2006.01)
*C12Q 1/58* (2006.01)

(56) References Cited

U.S. PATENT DOCUMENTS

| | | |
|---|---|---|
| 4,966,671 A | 10/1990 | Nylander et al. |
| 5,063,081 A | 11/1991 | Cozzette et al. |
| 5,096,669 A | 3/1992 | Lauks et al. |
| 5,112,455 A | 5/1992 | Cozzette et al. |
| 5,137,861 A | 8/1992 | Shih et al. |
| 5,200,051 A | 4/1993 | Cozzette et al. |
| 5,521,392 A | 5/1996 | Kennedy et al. |
| 5,554,339 A | 9/1996 | Cozzette et al. |
| 5,556,958 A | 9/1996 | Carroll et al. |
| 5,837,454 A | 11/1998 | Cozzette et al. |
| 5,945,570 A | 8/1999 | Arhancet et al. |
| 6,030,827 A | 2/2000 | Davis et al. |
| 6,049,008 A | 4/2000 | Roberts et al. |
| 6,306,594 B1 | 10/2001 | Cozzette et al. |
| 6,379,883 B2 | 4/2002 | Davis et al. |
| 6,423,381 B1 | 7/2002 | Colton et al. |
| 6,551,838 B2 | 4/2003 | Santini et al. |
| 6,615,078 B1 | 9/2003 | Burson et al. |
| 7,052,590 B1 | 5/2006 | Stigh et al. |
| 7,118,900 B2 | 10/2006 | Seul et al. |
| 7,169,290 B1 | 1/2007 | Aiken et al. |
| 7,540,948 B2 | 6/2009 | Collier et al. |
| 7,608,744 B1 | 10/2009 | Johnston et al. |
| 8,241,697 B2 | 8/2012 | Collier et al. |
| 2002/0068860 A1 | 6/2002 | Clark |
| 2002/0090738 A1 | 7/2002 | Cozzette et al. |
| 2003/0138842 A1 | 7/2003 | Seul et al. |
| 2003/0143570 A1 | 7/2003 | Abrams et al. |
| 2003/0144191 A1 | 7/2003 | Lee et al. |
| 2003/0166551 A1 | 9/2003 | Matsuzawa et al. |
| 2004/0203149 A1 | 10/2004 | Childs et al. |
| 2004/0231984 A1 | 11/2004 | Lauks et al. |
| 2004/0232049 A1 | 11/2004 | Dath et al. |
| 2005/0100685 A1 | 5/2005 | Flosbach et al. |
| 2005/0181993 A1 | 8/2005 | Creasey et al. |
| 2005/0205422 A1 | 9/2005 | Moser et al. |
| 2006/0046275 A1 | 3/2006 | Collier et al. |
| 2006/0134690 A1 | 6/2006 | Peters et al. |
| 2007/0015977 A1 | 1/2007 | McCann et al. |
| 2007/0027370 A1 | 2/2007 | Brauker et al. |
| 2007/0190331 A1 | 8/2007 | Charters et al. |
| 2008/0159442 A1 | 7/2008 | Tanabe et al. |
| 2008/0257784 A1 | 10/2008 | Dath et al. |
| 2009/0159442 A1 | 6/2009 | Collier et al. |
| 2010/0255120 A1 | 10/2010 | Collier et al. |
| 2012/0270756 A1 | 10/2012 | Collier et al. |

FOREIGN PATENT DOCUMENTS

| | | |
|---|---|---|
| JP | 57138389 A | 8/1982 |
| JP | S62-156561 | 7/1987 |
| JP | H04-503249 | 6/1992 |
| JP | 2000-065791 | 3/2000 |
| WO | WO 2006/028871 | 3/2006 |
| WO | 2006069579 A2 | 7/2006 |
| WO | WO 2006/086841 | 8/2006 |
| WO | WO 2009/082699 | 7/2009 |
| WO | 2010014153 A2 | 2/2010 |

OTHER PUBLICATIONS

Extended Search Report for European Appl. No. 08872669.0 dated Feb. 20, 2013.

Moser, et al., "Biosensor arrays for simultaneous measurement of glucose, lactate, glutamate, and glutamine", Biosensors and Bioelectronics, vol. 17, No. 4, Apr. 1, 2002, pp. 297-302.

Starodub, et al., "Liquid photopolymerizable compositions as immobilized matrix of biosensors", Bioelectrochemistry, vol. 71, No. 1, Sep. 14, 2007, pp. 29-32.

Song, et al., "Polymers of Microfluidic chips", Maccromolecular Research, vol. 14, No. 2, Apr. 30, 2006, pp. 121-128.

Mugweru, et al., "Electrochemical sensor array for glucose monitoring fabricated by rapid immobilization of active glucose oxidase within photochemically polymerized hydrogels", Journal of Diabetes Science and Technology, vol. 1, No. 3, May 1, 2007, pp. 366-371.

Japanese Office Action for JP Appl. No. 2010-539901 mailed Aug. 24, 2012.

Chinese Office Action for CN Appl. No. 200880126799.1 dated Oct. 18, 2012.

Bu et al., Analytical Chemistry, vol. 67, pp. 4017-4076, 1995.

Hayakwa, et al., "Efficacy of water-soluble photoinitiator on the adhesion of composite resin to bovine teeth in all-in-one system," Dental Materials Journal, vol. 24(2), pp. 213-218, 2005.

Hayakawa, et al., "Effectiveness of the addition of water-soluble photinitiator into the self-etching primers on the adhesion of a resin composite to polished dentin and enamel," Dental Materials Journal, vol. 18(3), pp. 324-333, 1999.

Rubio-Retama, et al., "High stability amperometric biosensor based on enzyme entrapment in microgels," Talanta, vol. 68, pp. 99-107, 2005.

Rozenzwieg and Kopelman, "Analytical properties of miniaturized oxygen and glucose fiber optic sensors," Sensors and Actuators B, vol. 35-36, pp. 475-483, 1996.

Kaltwasser and Schlegel, "NADH-dependent coupled enzyme assay for urease and other ammonia-producing systems," Analytical Biochemistry, vol. 16, pp. 132-138, 1966.

Notification of Transmittal of the International Search Report and the Written Opinion of the International Searching Authority for International Application No. PCT/US2010/022953, mailed Jul. 24, 2009.

Rehman, et al., "Immobilization of acrylamide-modified oligonucleotides by co-polymerization," Nucleic Acids Research, vol. 27, pp. 649-655, 1999.

Wall and Laidler, "The Molecular Kinetics of the Urea-Urease System: IV The Reaction in an Inert Buffer," Archives of Biochemistry and Biophysics, vol. 43, pp. 307-311, 1953.

D. Freifelder, "Physical Biochemistry: Applications to Biochemistry and Molecular Biology," Chapter 4, 2nd ed., 1982.

Wilber, et al., Journal of Biological Chemistry, vol. 176, pp. 147-154, 1948.

Amman, D., "Ion-Selective Microelectrodes," Springer, Berlin, p. 68, 1986.

Bernkop-Schnurch, et al., "Chemically Modified Chitosans as Enzyme Inhibitors," Advanced Drug Delivery Reviews, vol. 52, pp. 127-137, 2001.

Wolfbeis, et al., "Reversible Optical Sensor Membrane for Hydrogen Peroxide Using an Immobilized Fluorescent Probe, and it's Applicatoin to a Glucose Biosensor," Microchim. Acta., vol. 143, pp. 221-227, 2003.

Non-final Office Action for U.S. Appl. No. 11/961,498, dated Jan. 12, 2012.

Printout for glycerol from the Registry file of STN downloaded Dec. 31, 2011.

Office Action for U.S. Appl. No. 11/961,498 dated Aug. 1, 2011.

Office Action for corresponding Chinese Appl. No. 200880126799.1 dated Jun. 3, 2014.

International Search Report and Written Opinion for PCT/US2008/087730 dated Feb. 23, 2009.

International Preliminary Report on Patentability for PCT/US2008/087730 dated Jul. 1, 2010.

International Search Report and Written Opinion for PCT/US2010/022950 dated Sep. 7, 2011.

* cited by examiner

| Cartridge | Donor | Spike | RESIN | n | mV(mean) | SD |
|---|---|---|---|---|---|---|
| 6+ (BCL3-5) | 169M | WB | EIL | 5 | 5.67 | 0.22 |
| | | | Woodglue | 5 | 5.75 | 0.10 |
| | | Low Spike | EIL | 5 | 19.91 | 0.09 |
| | | | Woodglue | 5 | 19.20 | 0.22 |
| | | Hi Spike | EIL | 5 | 33.67 | 0.47 |
| | | | Woodglue | 5 | 32.00 | 0.20 |
| | 658F | WB | EIL | 5 | 0.47 | 0.17 |
| | | | Woodglue | 5 | 1.32 | 0.32 |
| | | Low Spike | EIL | 5 | 16.22 | 1.77 |
| | | | Woodglue | 5 | 15.26 | 1.22 |
| | | Hi Spike | EIL | 5 | 30.86 | 0.50 |
| | | | Woodglue | 5 | 29.51 | 0.17 |
| CHEM8+ (BCL4-5) | 169M | WB | EIL | 5 | 4.61 | 0.26 |
| | | | Woodglue | 5 | 4.31 | 0.18 |
| | | Low Spike | EIL | 5 | 19.67 | 0.23 |
| | | | Woodglue | 5 | 17.81 | 0.89 |
| | | Hi Spike | EIL | 3 | 33.16 | 0.23 |
| | | | Woodglue | 5 | 31.77 | 0.63 |
| | 658F | WB | EIL | 5 | -0.37 | 0.19 |
| | | | Woodglue | 5 | 0.77 | 1.24 |
| | | Low Spike | EIL | 2 | 17.46 | 0.05 |
| | | | Woodglue | 2 | 16.68 | 0.13 |
| | | Hi Spike | EIL | 5 | 30.65 | 0.12 |
| | | | Woodglue | 2 | 29.91 | 0.01 |

FIG. 5

|  | Final Amts (/ml volume) | |
|---|---|---|
| Reagent Component | amt | unit |
| Urease | 40 | mg |
| BSA | 22.32 | mg |
| Tris Buffer | 12.11 | mg |
| EDTA | 0.29 | mg |
| DTT | 0.15 | mg |
| glycerol | 28.57 | uL |
| sucrose | 71.39 | mg |
| acrylamide | 48.12 | mg |
| 2-hydroxy-1-[4-(2-hydroxyethoxy)phenyl]-2-methyl-1-propanone | 16.09 | mg |
| 1,4-Bis(acryloyl)piperazine | 19.62 | mg |
| Sodium Azide | 0.14 | mg |
| Water | 284.71 | uL |
| Sodium Cloride | 2.05 | mg |
| Potassium Chloride | 0.07 | mg |
| Aprotinin | 0.003 | mg |
| Total | 1000 | uL |

FIG. 14a

|  | Final Amts (/ml volume) | |
|---|---|---|
| Reagent Component | amt | unit |
| Urease | 40 | mg |
| Carbonic Anhydrase | 0.014 | mg |
| BSA | 22.32 | mg |
| Tris Buffer | 12.11 | mg |
| EDTA | 0.29 | mg |
| DTT | 0.15 | mg |
| glycerol | 28.57 | uL |
| sucrose | 71.39 | mg |
| acrylamide | 48.12 | mg |
| 2-hydroxy-1-[4-(2-hydroxyethoxy)phenyl]-2-methyl-1-propanone | 16.09 | mg |
| 1,4-Bis(acryloyl)piperazine | 19.62 | mg |
| Sodium Azide | 0.14 | mg |
| Water | 284.71 | uL |
| Sodium Chloride | 2.05 | mg |
| Potassium Chloride | 0.07 | mg |
| Aprotinin | 0.003 | mg |
| Total | 1000 | uL |

FIG. 14b

[1] 6110946a (M5) (acrylamide)
[2] 6110947c (M2) (PEGA)
[3] 6110948e (M4) (DMAPMA)
[4] 6110948f (M3) (methacrylamide)

[1] 6110944u (X6) (BAP)
[2] 6110939l (X1) (PEGDA)
[3] 6110943s (X4) (DHEBA)
[4] 6110940n (X5) (TMPETA)

| % glycerol | Day 1 | | Day 12 | |
|---|---|---|---|---|
| | 4° C | 40° C 50% RH | 4° C | 30° C |
| 0 | Good | FAIL | Poor | Fail |
| 2 | Good | Good | Good | Good |
| 10 | Good | Good | Good | Good |

Cartridge performance under different storage conditions and with lifetime

FIG. 17

FORMATION OF IMMOBILIZED BIOLOGICAL LAYERS FOR SENSING

FIELD OF THE INVENTION

An apparatus and method for manufacture of immobilized biological layers are disclosed.

The technology is capable of being used for sensing analytes in liquid samples in the point-of-care clinical diagnostic field and beyond. A curable composition of matter for the formation of immobilized biological layers is also disclosed.

BACKGROUND OF THE INVENTION

The development of miniaturized sensors for the measurement of biologically significant analyte species in biological fluids is becoming increasingly important, particularly because of the need for increasingly smaller devices that permit the measurement of such analyte species in the field or in the home. Notwithstanding advances in the field of sensor fabrication, there still exist major challenges in the miniaturization and fabrication of such sensors. One such challenge is the degree of complexity involved with the mass production of commercially viable sensors that comprise biological active molecules. Of major concern is the compatibility of the inherently harsh physical and chemical processes associated with existing semiconductor manufacturing methods, with sensitive organic compounds and labile biologically active molecules, both of which comprise parts of a functioning biological sensor. Another major challenge surrounding the miniaturization and fabrication of such sensors is the production of sensors that are sensitive and that can be made in mass quantities with a high degree of reproducibility. There is therefore a need for processes for forming sensors that take into account the sensitivity of the biologically active molecules used in the sensors, as well as the need for a highly uniform sensor when the sensor is produced in large quantities.

BRIEF DESCRIPTION OF THE DRAWINGS

The present invention will be better understood in view of the following non-limiting figures, wherein:

FIG. 2(a) the bare silver-silver chloride electrode 353; FIG. 2(b) as for (a) with a microdispensed ammonium ion-selective membrane 355; FIG. 2(c) as for (b) with an ultraviolet spot-cured acrylamide urease enzyme layer 356.

FIG. 3(a) shows an immobilized enzyme layer formed by the conventional ELVACE process (a vinyl acetate ethylene copolymer composed of hydrophilic and hydrophobic domains) process; FIG. 3(b) a UV spot-cured acrylamide urease enzyme layer with the desired uniform domed shape; and FIG. 3(c) a UV flood cured acrylamide urease enzyme layer;

FIG. 5 shows a sensor correlation data for acrylamide BUN sensors (EIL) of the type shown in FIG. 4, in whole blood (WB) for both a heated and un-heated chip compared to the ELVACE based (wood glue) enzyme immobilization membrane;

FIG. 14(a)-(b) show a table of reagents for matrix with preferred actual mixture compositions where FIG. 14(a) shows the components for the urease containing enzyme immobilization layer with urease as the only enzyme, and FIG. 14(b) is similar to 14(a) with the addition of carbonic anhydrase;

FIG. 17 shows data on the impact of the humectant at different concentrations with different shelf-life and storage conditions.

SUMMARY OF THE INVENTION

Figure 1:
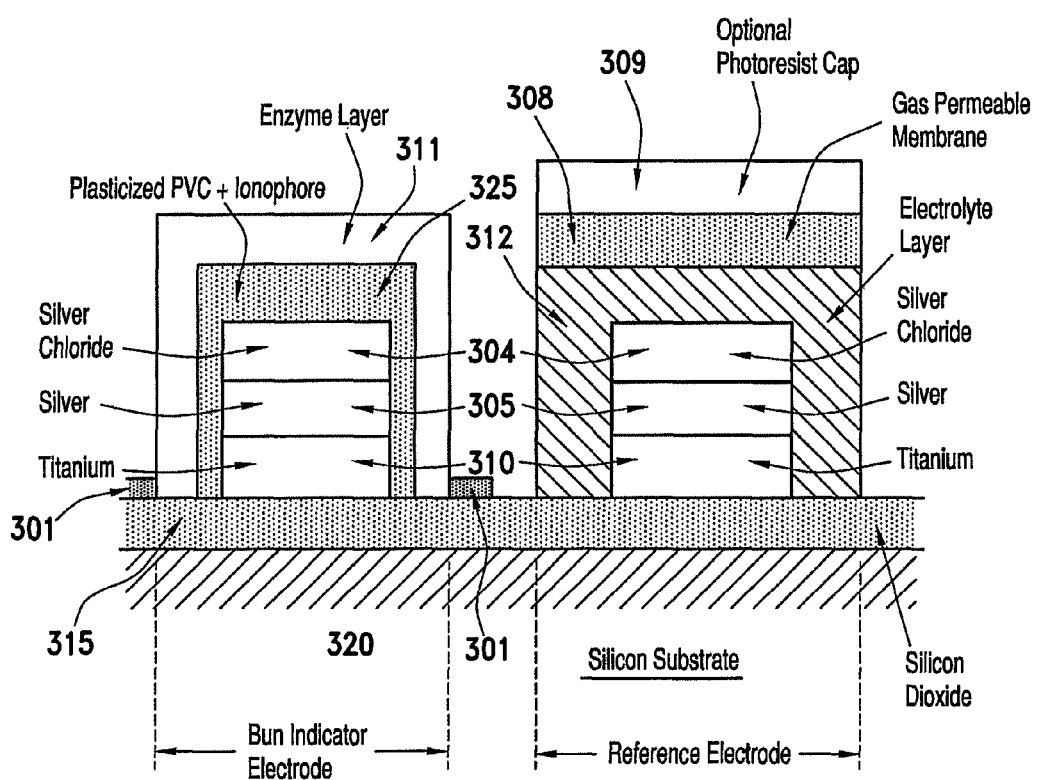
FIG. 1 shows a topological elevation cross-sectional view of a blood urea nitrogen (BUN) sensor fabricated on a silicon wafer in combination with a reference electrode.

The present invention provides an apparatus and method for the manufacture of immobilized biological layers for use in sensors for the measurement of biologically significant analyte species in biological fluids. The method and apparatus help produce devices with more uniform performance characteristics across a large manufacturing lot. An additional valuable feature of the method and apparatus is that they provide biological layers that substantially resist swelling when contacted with a liquid, such as, e.g., calibrant fluid, control fluid and blood. While not bound by any particular theory, it is believed that the biological layers produced using the method and apparatus resist swelling because there is a significant level of crosslinking in the layers. It has been found that a membrane that resists swelling in this way is desirable for the operation of the sensor, as biological layers that exhibit significant swelling can give inconsistent signals and even delaminate from the surface.

In one aspect, the invention is directed to a method of forming a sensor comprising the steps of: (a) forming a substantially homogeneous aqueous mixture comprising one or more enzymes, an acrylic-based monomer, a water soluble organic photo-initiator and a water soluble acrylic-based cross-linker in an aqueous mixture, (b) applying a controlled volume of said mixture onto a base sensor sufficient to cover said base sensor, and (c) exposing said applied volume to sufficient UV radiation to form an immobilized enzyme layer adhered to said base sensor.

Optionally, the enzyme is selected from the group consisting of urease, glucose oxidase, lactate oxidase, creatinase, creatininase, sarcosine oxidase, catalase, carbonic anhydrase, NAD(P)H oxidase, cholesterol oxidase, alcohol oxidase, choline oxidase, glycerol-3-phosphate oxidase, thiamine oxidase, pyruvate oxidase, pyridoxal oxidase, D-amino acid oxidase, L-amino acid oxidase, alkaline phosphatase, horseradish peroxidase and combinations thereof. The monomer may, for example, be selected from acrylamide, methacrylamide, N-[3-(dimethylamino)propyl]methacrylamide, hydroxyethylmethacrylate and combinations thereof. The organic photo-initiator may be selected from 2-hydroxy-1[4-(2-hydroxyethoxy)phenyl]-2-methyl-1-propanone, (insert means for claim 8) and combinations thereof. The cross-linker optionally is selected from 1,4-bisacryloyl piperazine, N,N'-(1,2-dihydroxyethylene)bis-acrylamide, N,N'-bis(acryloyl)cystamine, N,N'-methylenebisacrylamide, ethylene glycol diacrylate, (+)-N,N'-diallyltartramide and combinations thereof. The base sensor optionally is selected from the group consisting of electrode, ion-selective electrode, potentiometer electrode, amperometric electrode, conductimetric electrode, enzyme electrode, biosensor, optical sensor, fiber optic sensor, surface acoustic wave sensor, evanescent sensor, surface plasmon resonance sensor and optical wave guide sensor. In a preferred embodiment, the enzyme is urease and the base sensor is an ammonium ion-selective membrane.

The aqueous mixture optionally further comprises one or more stabilizing components selected from the group consisting of pH buffer, disulfide bond reducing agent, divalent ion chelating agent, protease inhibitor, bovine serum albumin, salts, biocide and humectant. The aqueous mixture optionally comprises urease, 2-hydroxy-1-[4-(2-hydroxyethoxy)phenyl]-2-methyl-1-propanone, bisacryloyl piperazine, glycerol and acrylamide monomer.

The method of applying the mixture may be by microdispensing a controlled volume in the range of about 5 nL to about 1 μL. The method of applying the mixture may be by means selected from the group consisting of spin-coating, dip-coating, spray coating, screen printing, ink jet printing, laser printing, painting and contact printing.

The UV radiation may be, for example, in the wavelength range of about 185 to 400 nm and optionally has an intensity in the range of about 100 to 400 mW/cm$^2$. said UV radiation step is a spot cure performed immediately after the dispensing step in a dispensing cycle. The UV radiation step optionally is a spot cure performed with a pre-selected time delay after the dispensing step, and may be performed for a duration of about 0.1 to 10 seconds.

In another embodiment, the invention is to a method of forming a urea sensor comprising the steps of: (a) forming a substantially homogeneous aqueous mixture comprising urease, glycerol, 2-hydroxy-1-[4-(2-hydroxyethoxy)phenyl]-2-methyl-1-propanone, bisacryloyl piperazine and acrylamide monomer, (b) dispensing a controlled volume of said mixture onto an ammonium ion-selective membrane sufficient to cover said membrane, and (c) exposing said dispensed volume to sufficient UV radiation to form an immobilized urease layer adhered to said membrane.

In another embodiment, the invention is to an apparatus for forming an immobilized enzyme layer on a substantially planar surface, the apparatus comprising a dispensing head for dispensing a controlled volume, e.g., in the range of about 5 nL to about 1 μL, of a photoformable enzyme-containing matrix at a pre-selected location on said surface and a UV radiation source, e.g., a mercury lamp, with a registration and alignment means capable of focusing a beam of radiation onto an area substantially covering said pre-selected location at a predetermined time and for a predetermined duration, at a predetermined intensity, after said matrix has been dispensed. Optionally, the apparatus further comprises a step and repeat means for changing the relative position of said surface with respect to said dispensing head and said UV radiation source for forming an array of immobilized enzyme layers at a set of pre-selected locations.

The substantially planar surface optionally is selected from a silicon wafer, alumina wafer, liquid crystal substrate, glass substrate and plastic substrate and flexible plastic substrate. The dispensing head may comprise, for example, a syringe needle with a reservoir for said matrix, and a displacement means for controlling the dispensed volume from said syringe onto said surface.

The photoformable matrix optionally is the composition comprising one or more enzymes, a humectant, an acrylic-based monomer, a water soluble organic photo-initiator and a water soluble acrylic-based cross-linker in a substantially homogeneous aqueous mixture.

The pre-selected location preferably has an area in the range of about 10 square microns to about 75 square millimeters. Optionally, the pre-selected location is substantially circular and has radial dimensions in the range of about 5 pm to about 5 mm.

Optionally, registration and alignment means permit the beam to be focused on a selected area of said surface and illuminate an area in the range of about 10 square microns to about 75 square millimeters. A computer program may control the timing and location of dispensing and/or the timing and location of the application of UV radiation with respect to the timing of dispensing.

Optionally, the dispensing head is capable of dispensing a sequence of controlled volumes of a photoformable matrix at a pre-selected set of locations on said surface, and said UV radiation source is capable of focusing a beam of radiation onto an area substantially covering each said pre-selected locations, in sequence at a predetermined time after each controlled volume is dispensed, for a predetermined duration.

In another embodiment, the invention is to an apparatus for forming an array of immobilized enzyme layers on an array of sensors on a substantially planar surface comprising: a dispensing head for dispensing a sequence of controlled volumes of a photoformable enzyme-containing matrix at a pre-selected set of locations on said surface, and a UV radiation source with a registration and alignment means capable of focusing a beam of radiation onto an area substantially covering each said pre-selected location, in sequence at a predetermined time after each controlled volume is dispensed, for a predetermined duration.

In another embodiment, the invention is to a method of forming an immobilized layer on a sensor on a substantially planar surface comprising the steps of: (a) dispensing a controlled volume of a photoformable matrix at a pre-selected location on said surface, wherein the photoformable matrix comprises a biologically active material; and (b) applying a UV radiation beam onto an area substantially covering said pre-selected location, starting at a predetermined time after said volume has been dispensed and for a predetermined duration at a predetermined intensity, to form said immobilized layer.

The photoformable matrix optionally comprises one or more enzymes, an acrylic-based monomer, a water soluble organic photo-initiator and a water soluble acrylic-based cross-linker in an aqueous mixture. The biologically active material optionally is selected from the group consisting of protein, enzyme, antibody, antibody fragment, RNA, single stranded DNA and double stranded DNA. The immobilized layer preferably is an enzyme layer.

In another embodiment, the invention is to a method of forming an array of immobilized layers on an array of sensors on a substantially planar surface comprising the steps of: (a) dispensing a sequence of controlled volumes of a photoformable matrix at a pre-selected set of locations on said surface, and (b) applying a UV radiation beam onto an area substantially covering each said pre-selected location, in sequence, starting at a predetermined time, e.g., in the range of about 0.1 to about 10 seconds, after each controlled volume has been dispensed, and applying said radiation at a predetermined intensity for a predetermined duration, e.g., in the range of about 0.1 to about 10 seconds, to form said immobilized array of layer. The UV radiation preferably is in the wavelength range of about 185 to 400 nm and the UV radiation intensity may be in the range of about 100 to 400 mW/cm². The planar surface optionally is a silicon wafer and the pre-selected set of locations is an array of sensors on said wafer. The UV radiation beam optionally is applied to the Nth minus X pre-selected location while dispensing occurs at the Nth pre-selected location, where X is equal to an integer from 1 to 10.

In another embodiment, the invention is to a sensor, comprising an electrode with a first layer covering said electrode comprising an ion-selective membrane, and a second layer covering said ion-selective membrane comprising a UV cured matrix formed from a substantially homogeneous aqueous mixture of one or more enzymes, a humectant, an acrylic-based monomer, a water-soluble organic photo-initiator and a water-soluble acrylic-based cross-linker.

DETAILED DESCRIPTION OF THE INVENTION

In one aspect, the invention relates to an enzyme immobilization composition comprising one or more enzymes, a humectant, an acrylic-based monomer, a water-soluble organic photo-initiator and a water-soluble acrylic-based cross-linker in a substantially homogeneous aqueous mixture.

Enzymes

The one or more enzymes included in the composition of the present invention may vary widely. In some embodiments, the one or more enzymes comprises urease. The enzyme urease is particularly well suited for incorporation into biosensors that quantify the blood urea nitrogen (BUN) content in an assay. BUN assays are useful in measuring the levels of urea nitrogen, a waste product of protein metabolism that is cleared by the kidneys, in the blood. BUN assays therefore assess renal function. Clinically useful BUN values are 2-140 mg/100 mL (dL). The condition known as azotemia, i.e., increased BUN levels, can indicate impaired renal function, congestive heart failure, dehydration, shock, hemorrhage into the gastrointestinal tract, stress, acute myocardial infarction or excessive protein intake. Alternatively, decreased BUN values may indicate liver failure, malnutrition, anabolic steroid use, pregnancy and siliac disease.

Urea in whole blood is detected in a two-step process. First, the urea is enzymatically converted to the products $NH_4^+$ and $HCO_3^-$ in "the urease reaction" via a mechanism that is not well understood. The second step in the detection of urea is the potentiometric determination of ammonium ion activity by the $NH_4^+$ ion-selective electrode (ISE). See, D. Freifelder, *Physical Biochemistry: Applications to Biochemistry and Molecular Biology* Chapter 4 (2d ed. 1982). The BUN sensor response, i.e., change in potential due to changes in the concentration of $NH_4^+$, is calibrated at known levels of urea in blood. A plot of a sensor response curve, (chronopotentiometric graph in millivolts as a function of time), thus can be used to indicate the concentration of ammonium ion within the sensor membrane, which provides an estimate indirectly of the urea concentration in the blood.

Since the enzymatic breakdown of urea by urease produces the species $H^+$ and $CO_2$ as byproducts from the decomposition of $HCO_3^-$, the BUN content can be determined using sensors that detect changes in the $H^+$ or $CO_2$. Detection of ammonium ion is preferred because of the relatively low background concentration of ammonium ions in the blood. In contrast, blood has a significant background of $H^+$, $CO_2$ and $HCO_3^-$. The production of ions during the urease reaction also increases the conductivity of the sample, which can be detected with a conductivity sensor.

An ideal property of urease is that it has a low residual level of associated product (ammonium ions <0.00001 mol/enzyme unit) and other nitrogenous compounds. The urease that is used in the enzyme immobilization compositions of the present invention should ideally be free of contaminating proteases and should have specific activities greater than 500 U/mg protein at 25° C. In addition, the enzyme should also be of high purity. In some embodiments, the urease should have a $K_m$ in the range of from about 1 to about 100 mM, e.g., from about 1 to about 50 mM or from about 25 to about 75 mM, and preferably about 50 mM. In addition, the urease should have a $V_{max}$ greater than 16,000 (micromol/ml/min). Finally, the urease should have a $K_{cat}$ of about $5 \times 10^5$ min$^{-1}$ or greater.

In a preferred embodiment, the urease is Jack Bean urease (E.C. 3.5.1.5) (Biozyme Laboratories, San Diego, Calif.). Other sources of Jack Bean Urease (E.C. 3.5.1.5) include; (i) Sigma-Aldrich Canada Ltd. (Oakville, Ontario, Canada); (ii) Toyobo (Tokyo, Japan); (iii) Worthington Biochemical Corporation (Lakewood, N.J.), (iv) Genzyme Diagnostics (Cambridge, Mass.).

In some embodiments the enzyme immobilization compositions of the present invention comprise carbonic anhydrase and urease. Carbonic anhydrase converts bicarbonate formed by the urease reaction to carbon dioxide, thereby increasing the rate of ammonium ion production as described in U.S. patent application Ser. No. 11/216,041, the entirety of which is incorporated herein by reference. The carbonic anhydrase that is used in these compositions should ideally have low residual levels of nitrogenous compounds, be free of contaminating proteases and should otherwise be of high purity. In addition, the carbonic anhydrase should have a specific activity greater than 2500 Wilbur-Anderson units/mg protein at 0° C. (Wilber, K. M. and N. G. Anderson, *Journal of Biological Chemistry* 176: 147-154 (1948)). In some embodiments, the carbonic anhydrase should have a $K_m$ value between 1 to 50 mM, where the preferred $K_m$ is 1 to 5. In addition, the carbonic anhydrase should have a $V_{max}$ greater than 50 (microl/ml/min), preferably above 10,000 (microl/ml/min). Finally, the carbonic anhydrase should have a $K_{cat}$ value greater than 75 min$^{-1}$, preferably greater than $5 \times 10^5$ min$^{-1}$.

In a preferred embodiment, the carbonic anhydrase is bovine carbonic anhydrase (E.C. 4.2.1.1) (Sigma-Aldrich Canada Ltd., Oakville, Ontario, Canada; $K_m$: 1.31 mM; $V_{max}$: 64.4 Micromol/ml/min; $K_{cat}$: 76.24 min$^{-1}$). Another source of Bovine carbonic anhydrase (E.C. 4.2.1.1) is Worthington Biochemical Corporation (Lakewood, N.J.).

Although in some preferred embodiments, the enzyme used in the enzyme immobilization compositions of the present invention is urease, any other enzyme that is compatible with the immobilization compositions can be used individually or in combination with another enzyme (e.g., urease and carbonic anhydrase). In some embodiments, the enzyme can be selected from the group consisting of glucose oxidase, lactate oxidase, creatinase, creatininase, sarcosine oxidase, catalase. NAD(P)H oxidase, cholesterol oxidase, alcohol oxidase, choline oxidase, glycerol-3-phosphate oxidase, thiamine oxidase, pyruvate oxidase, pyridoxal oxidase, D-amino acid oxidase, L-amino acid oxidase, urease, alkaline phosphatase, horseradish peroxidase and combinations thereof. It can be appreciated that the enzyme used determines the analyte that is being sensed. Thus, for example, glucose oxidase can be used in a sensor to detect glucose; lactate oxidase can be used to detect lactate; and a combination of urease and carbonic anhydrase can be used for the simultaneous detection of BUN content.

Monomers, Photo-Initiators and Cross-Linkers

As discussed above, the enzyme immobilization compositions of the present invention comprise an acrylic-based monomer, a water-soluble organic photo-initiator and a water-soluble acrylic-based cross-linker. In some embodiments, the acrylic-based monomer comprises an acrylamide. In other embodiments, the monomer comprises a methacrylamide, poly(ethylene glycol) acrylate, N-[3-(dimethylamino)propyl] methacrylamide, hydroxyethylmethacrylate, or mixtures thereof.

The organic photo-initiator can be any photo-initiator that is capable of polymerizing a monomer. In some embodiments, the photo-initiator is selected from the group consisting of 2,6-bis(4-azidobenzylidene)cyclohexanone; 2,6-bis(4-azidobenzylidene)-4-methylcyclohexanone; 4,4-diazidostilbene-2,2'-disulfonic acid disodium salt; ammonium dichromate; 1-hydroxy-cyclohexyl-pentyl-keton (Irgacure 907); 2-methyl-1[4-(methylthio)phenyl]-2-morpholinopropane-1-one (Irgacure 184C); 2-hydroxy-2-methyl-1-phenyl-propane-1-one(Darocur 1173); a mixed photo-initiator (Irgacure 500) of 50 wt % of Irgacure 184C and 50 wt % of benzophenone; a mixed initiator (Irgacure 1000) of 20 wt % of Irgacure 184C and 80 wt % of Darocur 1173; 2-hydroxy-1-[4-(2-hydroxyethoxy)phenyl]-2-methyl-1-propanone (Irgacure 2959); methylbenzoylformate (Darocur MBF); alpha, alpha-dimethoxy-alpha-phenylacetophenone (Irgacure 651); 2-benzyl-2-(dimethylamino)-1-[4-(4-morpholinyl)phenyl]-1-butanone (Irgacure 369); a mixed initiator (Irgacure 1300) of 30 wt % of Irgacure 369 and 70 wt of Irgacure 651; diphenyl (2,4,6-trimethylbenzoyl)-phosphine oxide (Darocur TPO); a mixed initiator (Darocur 4265) of 50 wt % of Darocur TPO and 50 wt % of Darocur 1173; a phosphine oxide; phenyl bis(2,4,6-trimethyl benzoyl) (Irgacure 819); a mixed initiator (Irgacure 2005) of 5 wt % of Irgacure 819 and 95 wt % of Darocur 1173; a mixed initiator (Irgacure 2010) of 10 wt % of Irgacure 819 and 90 wt % of Darocur 1173; a mixed initiator (Irgacure 2020) of 20 wt % of Irgacure 819 and 80 wt % of Darcocur 1173; bis (etha 5-2,4-cyclopentadiene-1-yl) bis[2,6-difluoro-3-(1H-pyrrole-1-yl) phenyl]titanium (Irgacure 784); a mixed initiator containing benzophenone(HSP 188); and derivatives thereof. In a preferred embodiment, the photo-initiator comprises 2-hydroxy-1-[4-(2-hydroxyethoxy)phenyl]-2-methyl-1-propanone. In other embodiments, the photo-initiator comprises 2-hydroxy-3-(3,4-dimethyl-9-oxo-9H-thioxanthen-2-yloxy)-N,N,N-trimethy-1-propanaminium chloride. Additionally these photo-initiators may be used in combination.

In a preferred embodiment the cross-linker is any chemical entity that is able to promote the cross-linking of the polymer formed from the monomer. In one embodiment, the cross-linker comprises 1,4-bisacryloyl piperazine (BAP). In other embodiments, the cross-linker comprises N,N'-(1,2-dihydroxyethylene)bis-acrylamide, N,N'-bis(acryloyl)cystamine, N,N'-methylenebisacrylamide, poly (ethylene glycol) diacrylate, trimethylolpropane ethoxylate triacrylate, (+)-N,N'-diallyltartramide, or mixtures thereof.

Humectants, Buffers and Other Components

In addition to the acrylic-based monomer, water-soluble organic photo-initiator and water-soluble acrylic-based cross-linker, the enzyme immobilization matrix can optionally further comprise other stabilizing components that include, e.g., a pH buffer, a disulfide bond reducing agent, a divalent ion chelating agent, a protease inhibitor, an albumin, a salt, a sugar, a biocide, a humectant and a plasticizer. In a preferred embodiment the enzyme immobilization matrix comprises TRIS buffer, bisacrylamide, dithiothreitol, ethylene diamine tetraacetate, sucrose, aprotinin, bovine serum albumin, sodium chloride, potassium chloride, sodium azide and glycerol. See FIG. 14.

In some embodiments, the compositions of the present invention comprise a humectant. When a humectant is added, it is preferably selected from glycerol, propylene glycol, glyceryl triacetate, sorbitol, xylitol, maltitol, polydextrose, quillaia, lactic acid, lithium chloride and 1,2-propanediol. In one embodiment, the concentration of humectant in the composition is on the order of 2-20%, e.g., about 2-15%, about 2-10% or about 2-8% (v/v). In some cases, it has been found that at too high of a concentration, the humectant can reduce product shelf-life. Humectants, e.g., glycerol, are added to prevent the matrix from drying during the microdispensing process and prior to the curing step. If the microdispensed drop dries too soon, the components of the formulation can precipitate out of solution and this can adversely affects cross-linking and curing. As a result of the small size of the drops dispensed onto a substrate, microdispensed in a low humidity manufacturing environment, is easily prone to rapid drying. Accordingly, it is important to control the ambient temperature and humidity. Preferable ranges for the processes described here are 4 to 25° C. and 5 to 30% relative humidity.

The formulations of the present invention preferably comprise biochemical buffer components useful for maintaining and optimizing the enzymatic activity. Exemplary buffers include tris(hydroxymethyl)aminomethane (TRIS), sodium barbital, 4-(2-hydroxyethyl)-1-piperazineethanesulfonic acid (HEPES), piperazine diethanesulfonic acid (PIPES), 2-(N-morpholino)ethanesulfonic acid (MES), 3-(N-morpholino)propanesulfonic acid (MOPS), Tricine, BIS-TRIS, phosphate, phosphate-saline, saline sodium citrate (SSC), saline sodium phosphate ethylene diamine tetraacetic acid (SSPE), N-tris(hydroxymethyl) methyl-3-aminopropanesulfonic acid (TAPS), tris acetate ethylene diamine tetraacetic acid (TAE), tris borate ethylene diamine tetraacetic acid (TBE), and mixtures thereof. In a preferred embodiment, the buffer is TRIS.

In some embodiments, the compositions of the present invention optionally comprise a reducing agent. Exemplary reducing agents include dithiothreitol (DTT), 2-mercaptoethanol, tris(2-carboxyethyl)phosphine HCl, dithioerythritol, glutathione and mixtures thereof. In a preferred embodiment, the reducing agent is DTT. It may be advantageous to add a reducing agent to the compositions of the presenting invention to prevent enzymes comprised in the compositions from forming inactive multimers.

In some embodiments, the compositions of the present invention optionally comprise a cation binder, preferably, a divalent cation binder. Exemplary divalent cation binders include ethylene diamine tetraacetic acid (EDTA), sodium citrate, ethylene glycol tetraacetic acid, diethylene triamine pentaacetic acid, ethylenediamine, and mixtures thereof. Such cation binders are added as metal chelators to prevent metal ion inactivation, as well as to prevent the activation of proteases.

In some embodiments, the compositions of the present invention comprise a protease inhibitor. Exemplary protease inhibitors include aprotinin, chicken egg white cystatin, antipain, cystamine dihydrochloride, chymostatin, 3,4-dichloroisocoumarin, E-64, ebselen, Gly-Gly-Tyr-Arg synthetic peptide, leupeptin, alpha2-macroglobulin, N-alpha-tosyl-L-lysine chloromethyl ketone hydrochloride, N-alpha para tosyl-L-phenylalanine chloromethyl ketone hydrochloride, pepstatin A, pesinostreptin, epsilon-amino-n-caproic acid, 4-(2-aminoethyl) benzenesulfonyl fluoride hydrochloride, antithrombin III, bdellin, complement C1 esterase inhibitor, 3,4-dichloroisocoumarin, diisopropyl fluorophosphage, elastatinal, gabexate mesylate, leupeptin, alpha2-macroglobulin, N-acetyl-glu-ser-met-asp-al, N-acetyl-ile-gly-thr-asp-al, diisopropyl fluorophosphates, Na-T-Boc-deacetylleupeptin, acetyl-pepstatin, histatin 5, Cbz-Leu-Leu-Phe-al, Cbz-Leu-Leu-Leu-B(OH)$_2$, lactacystin, clasto-lactacystin beta-lactone, diisopropyl fluorophosphates, phenylmethylsulfonyl fluoride, pepstatin A, D-His-Pro-Phe-His-Leu-psi-(CH$_2$NH)-Leu-Val-Tyr, diethylenetriaminepentaacetic acid, 1,10-phenanthroline monohydrase, phosphoramidon, diisopropyl fluorophosphates, N-acetyl-eglin C, gabexate mesylate, hirudin, N alpha-(2-naphthalenesulfonylglycyl)-4-amidino-DL-pheylalaninepiperidide, D-Val-Leu-Lys-chloromethyl ketone, para-anlinobenzamidine dihydrochloride, ecotin, trypsin inhibitor, trypsin-chymotrypsin inhibitor and Glu-Gly-Arg-chloromethyl ketone. In a preferred embodiment, aprotinin is added as a protease inhibitor for any protease that may contact the membrane at the time of blood sample analysis and also may be present in the matrix formulation which would affect product shelf-life.

In some embodiments, the compositions of the present invention comprise a biocide. Exemplary biocides include sodium azide, 2-methyl-4-isothiazolin-3-one, 5-chloro-2-methyl-4-isothiazolin-3-one, thimerosal, hypochlorite, and mixtures thereof. In a preferred embodiment, sodium azide is added as a biocide for prophylactic protection of the formulation from microorganisms either before or after spot curing.

In some embodiments, the compositions of the present invention comprise a plasticizer.

Exemplary plasticizers include glycerol, propylene glycol, polyethylene glycol, and mixtures thereof. In a preferred embodiment, the plasticizer is glycerol. It should be appreciated that some plasticizers, e.g., glycerol, can act both as plasticizers and as humectants, thus making the compositions of the present invention more flexible. This prevents the cured acrylic resin from cracking and delaminating during temperature changes and other conditions that might place the material under stress, known as environmental stress cracking (ESC).

In some embodiments, the compositions of the present invention comprise a salt. Exemplary salts include sodium chloride, potassium chloride, sodium phosphate, potassium phosphate, and mixtures thereof. The addition of a low concentration of salts, preferably sodium chloride and potassium chloride, was found to reduce the rate of delamination, i.e., loss of membrane adhesion when subsequently contacting a calibrant fluid or blood sample. While not being bound by any theory, this improvement is believed to be due to the reduction in the difference in osmotic concentrations between the sample and the membrane with the addition of endogenous salt. As the ion selective electrode (ISE) is sensitive to sodium and potassium ions, the concentration was optimized to reduce this background impact on the ISE. In some embodiments, the salt concentration is from about 0.1 mM to about 140 mM, e.g., from about 30 mM to about 140 mM, from about 0.1 mM to about 1 mM, from about 20 mM to about 50 mM, or from about 20 mM to about 40 mM. In a preferred embodiment, the compositions of the present invention comprise 0.9 mM KCl and 35 mM NaCl is used.

In some embodiments, the compositions of the present invention comprise an anhydrobiotic protectant. Exemplary anhydrobiotic protectants include sucrose, trehalose, mannitol and mixtures thereof. In a preferred embodiment, the anhydrobiotic protectant is sucrose. Sucrose is preferably added as an anhydrobiotic protectant, to enhance membrane stability so that the test cartridge in which the sensor is packaged exhibits an extended shelf-life, e.g., 6-12 months or longer. Bovine serum albumin (BSA) can also be added as it was observed to increase cartridge shelf-life and ensure good membrane adhesion.

Preparation of Compositions

In some embodiments, the compositions of the present invention are mixed, aliquoted and then stored frozen, until an aliquot is thawed and used for microdispensing. In a preferred embodiment, the monomer (e.g., acrylamide) and the cross-linker (e.g., BAP) are mixed together in solution. To the monomer/cross-linker solution is added the photoinitiator (e.g., Irgacure 2959). In some embodiments, it is desirable to add the photo-initiator last, as it is the most reactive and this precaution reduces its exposure to light. In a preferred embodiment samples were frozen at −60° C. and found to be stable for at least 4 months. Sample freezing can range from −20 to −120° C. where colder temperatures are preferable. At these cryogenic temperatures, the formulation can remain stable for several years.

While the compositions of the present invention are preferably used to immobilize enzymes, those skilled in the art will recognize that they can also be used to immobilize other biologically active materials, instead of, or as well as enzymes, e.g., antibodies, antibody fragments, RNA, single stranded DNA and double stranded DNA. See, e.g., Rehman et al., 1999, "Immobilization of acrylamide-modified oligonucleotides by co-polymerization," *Nucleic Acids Research*, 27: 649-655 (1999), which is incorporated herein by reference.

When formulating the enzyme immobilization compositions of the present invention, it is necessary to consider both solubility and buffering of the composition. Enzymes generally require an aqueous buffered solution near pH 7, but there are exceptions, e.g., alkaline phosphatase. For example, the optimum pH for urease is reported 8.0 (Wall & Laidler, The Molecular Kinetics of the Urea-Urease System: IV The Reaction in an Inert Buffer, *Archives of Biochemistry and Biophysics* 43: 307-311 (1953)). It has been found, however, that in order to obtain an optimal enzyme activity in the compositions of the present invention, it is advantageous to use a pH less than pH 8.0. In some embodiments the pH of the compositions of the present invention is from about 6.5 to about 7.4. The pH of the compositions may be maintained in that range by using well known buffers. An exemplary buffer includes, but is not limited to 100 mM TRIS, at pH 7.6. TRIS buffers ranging from 10 to 200 mM can also be used in the pH range from about pH 6.5 to about 8.0. Other buffers useful in the present invention include sodium phosphate, potassium phosphate, TRIS (trishydroxymethylaminomethane), e.g., TRIS-$H_2SO_4$, HEPES, TRIS-HCl buffer and barbitone.

Most photo-initiators also have limited solubility in aqueous based solvents. Additionally, acrylic resin cross-linkers are also only slightly soluble in aqueous solutions. For example, the photo-initiator 2-hydroxy-1-[4-(2-hydroxyethoxy)phenyl]-2-methyl-1-propanone, when dissolved in an acrylic resin solution comprising a monomer and a cross-linker, was found to be slightly more soluble and could be dissolved into the aqueous solution. Higher concentrations of photo-initiator are preferred. It is important, however, that the photo-initiator does not precipitate out of solution. Accordingly, identifying an appropriate concentration range is important. In some embodiments, the concentration range of photo-initiator is from about 0.5 to about 10%, e.g., from about 0.5 to about 5%, or from about 0.5 to about 4.0%.

Figure 2A:
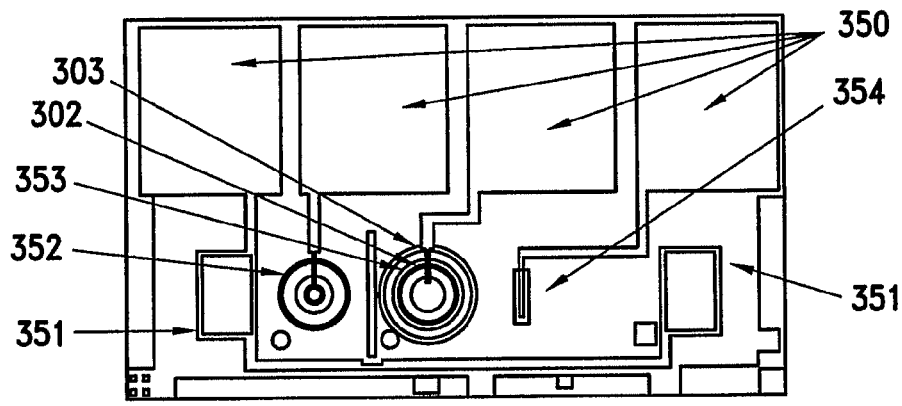
FIGS. 2(a)-(c) show plan views of a BUN sensor on a silicon chip (2 mm×3 mm) at different steps of manufacture, as follows.
Figure 2B:
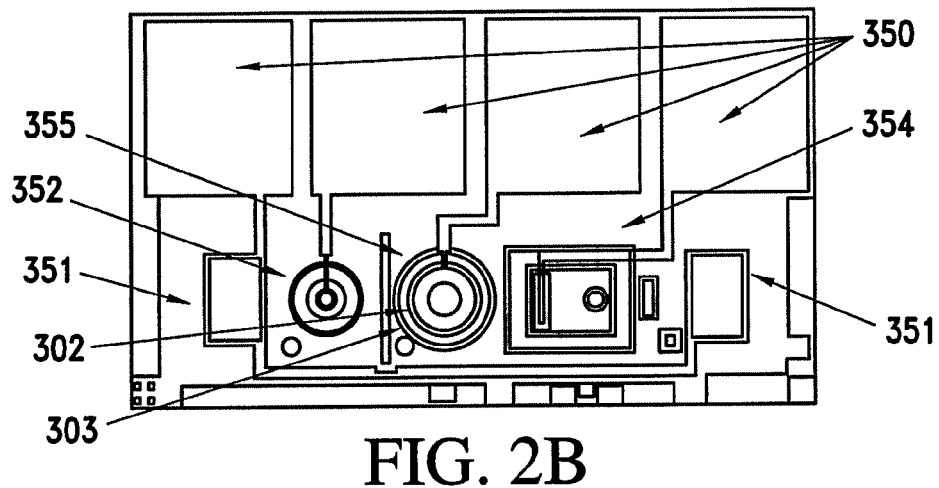
Figure 2C:
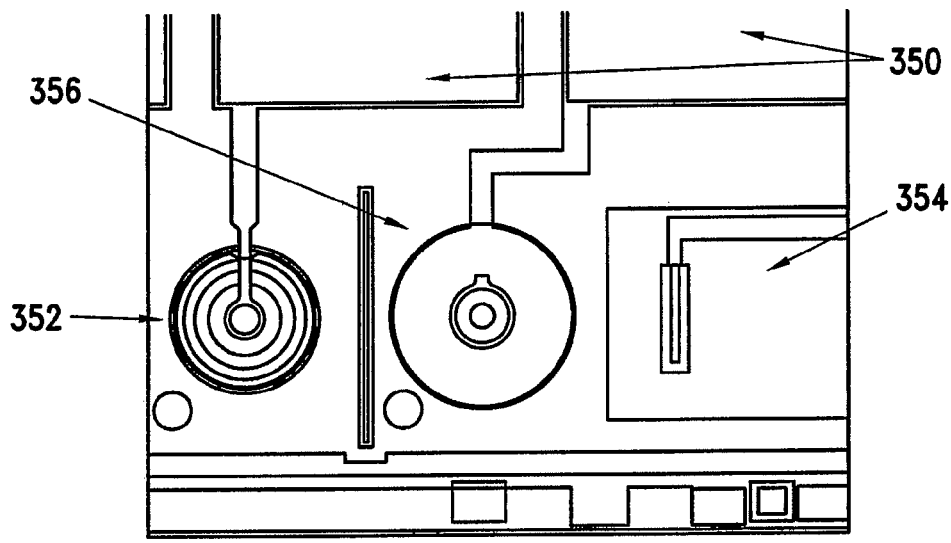
Figure 3A:
FIGS. 3(a)-(c) show electron micrograph views of finished BUN sensors, as follows.
Figure 3B:

A microdispensed layer of the preferred matrix comprising urease, 2-hydroxy-1-[4-(2-hydroxyethoxy)phenyl]-2-methyl-1-propanone, bisacryloyl piperazine and acrylamide monomer is shown in FIGS. 2(c) and 3(b). The matrix is dispensed in a controlled volume onto an ammonium ion-selective membrane (see FIG. 2(b)) sufficient to cover the membrane, and then exposed to sufficient UV radiation to form an immobilized urease layer adhered to the membrane. The nominal volume of the microdispensed matrix is preferably about 50 nL, but a wide range of volumes can be used. For sensors with the dimensions shown in FIG. 2, the range is preferably 10-200 nL.

FIG. 3 shows scanning electron micrographs (SEMs) that illustrate typical prints created using different protocols. With spot-curing (see FIG. 3(b)), each microdispensed drop is exposed to UV at a predetermined time interval after the microdispensing event. Control of the time domain for each individual printed membrane was as follows for FIG. 3(b): $t_0$ dispense membrane, $t_1$ apply UV, $t_2$ stop UV, where $t_0$ to $t_1$ is 0.5 second and $t_1$ to $t_2$ is 0.6 second. For the immobilized enzyme layer shown in FIG. 3(b), the UV radiation wavelength was 310 nm, and the UV intensity was 2 W/cm². Preferably, the dispense membrane matrix step $t_0$ to $t_1$ ranges from about 0.05 to about 2.0 seconds, e.g., from about 0.1 to about 1.0 seconds. The UV radiation step preferably ranges from about 0.05 to 120 seconds, e.g., from about 0.1 to about 60 seconds. The UV radiation wavelength can vary, for example, from about 260 to about 360 nm, and preferably is specific to the photoinitiator. Preferably, with 2-hydroxy-1-[4-(2-hydroxyethoxy)phenyl]-2-methyl-1-propanone photo-initiator, the UV wavelength is 310 nm. The UV radiation intensity can vary from about 0.005 to about 50 W/cm², e.g., from about 0.01 to about 10 W/cm². The UV radiation intensity and time are related characteristics of the process, wherein a reduction in one typically necessitates an increase in the other parameter. Further, shorter wavelengths of UV radiation can have a negative impact on sensitive biological materials. Accordingly, wavelengths above about 300 nm are preferred.

Figure 3C:
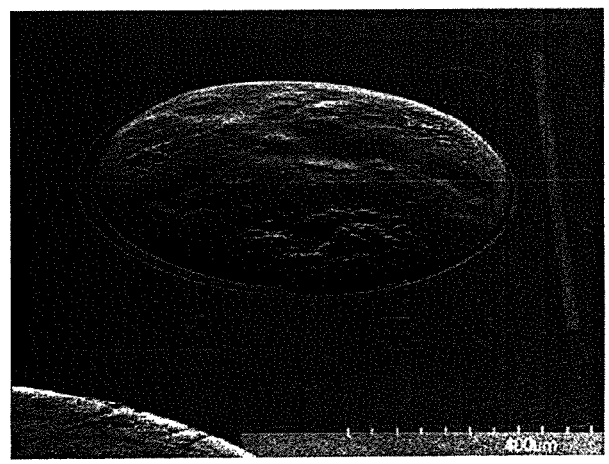

By way of comparison, FIG. 3(c) depicts a curing step using a flood UV system. The UV flood cure system requires that all the drops of matrix are microdispensed onto a substrate, e.g., a wafer, before the flood curing step is executed. This means that the earlier drops dry (or set-up) for longer than the later drops. This delay can lead to time-dependent variations in the cured structure. Given the small dimensions of the printed drops, they can dry quickly with the components becoming insoluble, and thus are less amenable to being UV cured. For comparison, FIG. 3(a) shows an enzyme layer formed by the conventional ELVACE process. "ELVACE" is a vinyl acetate ethylene copolymer composed of hydrophilic and hydrophobic domains. The ELVACE process does not involve a UV curing step. It is noted that the variable surface using the ELVACE structure may undesirably contribute to performance variability, as can the structure shown in FIG. 3(c).

Figure 4:
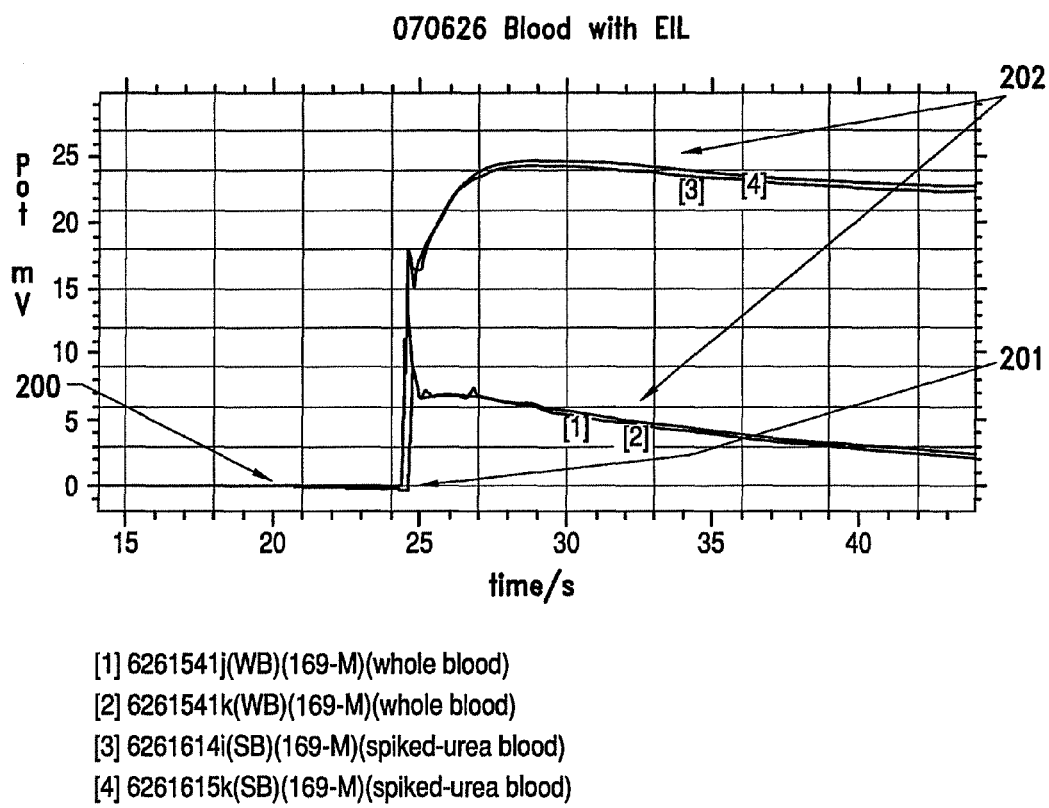
FIG. 4 shows a sensor output data (chronopotentiometric graph) for an acrylamide BUN sensor using the composition described in FIG. 14(a), in going from calibrant fluid to blood.

It has been found that the UV spot cure process provides the most consistent domed structures, as shown in FIG. 3(b), and surprisingly and unexpectedly yields superior sensor performance characteristics. FIG. 4 shows typical sensor output data for a spot-cured acrylamide BUN sensor, in going from calibrant fluid to blood, and FIG. 5 shows typical sensor correlation data for the spot-cured acrylamide BUN sensor in blood. Note that these structures are also more robust mechanically having superior adhesion compared to the other structures.

In FIG. 4, the chronopotentiometric graph shows the potential difference when the calibrant solution is measured at time point 200, and then a test sample or in this case two different blood samples with a low and high urea concentration, are added to the sensor at time point 201. After a short time for the sensor output to stabilize, the potential difference is measured at time point 202. The difference between the potential at time points 202 and 201 can be used to determine the urea concentration in the sample. This is based on the Nernst equation where the slope and intercept are empirically determined. The change in voltage at time points 202 and 201 can be semi-log plotted against the logarithm of analyte concentration giving a graph with a linear response to voltage based on the analyte concentration.

In FIG. 5 the new UV cured enzyme immobilization layer (EIL) is compared to the prior art enzyme formulated in ELVACE (also termed a film-forming latex). Experiments used two different biosensor chips, one heated (BCL4-5) and the other un-heated (BCL3-5). Two different blood donor samples, 169M (male) and 658F (female) were used. Some samples were tested without spiking with additional urea, and others were amended by adding urea, identified as low spike and high spike. Five cartridges were built for each test condition and the raw potential difference in mV was recorded. The standard deviation (SD) of the 5 samples was calculated for each sample tested. These data showed comparable standard deviation to the prior art ELVACE-based process.

Figure 18:
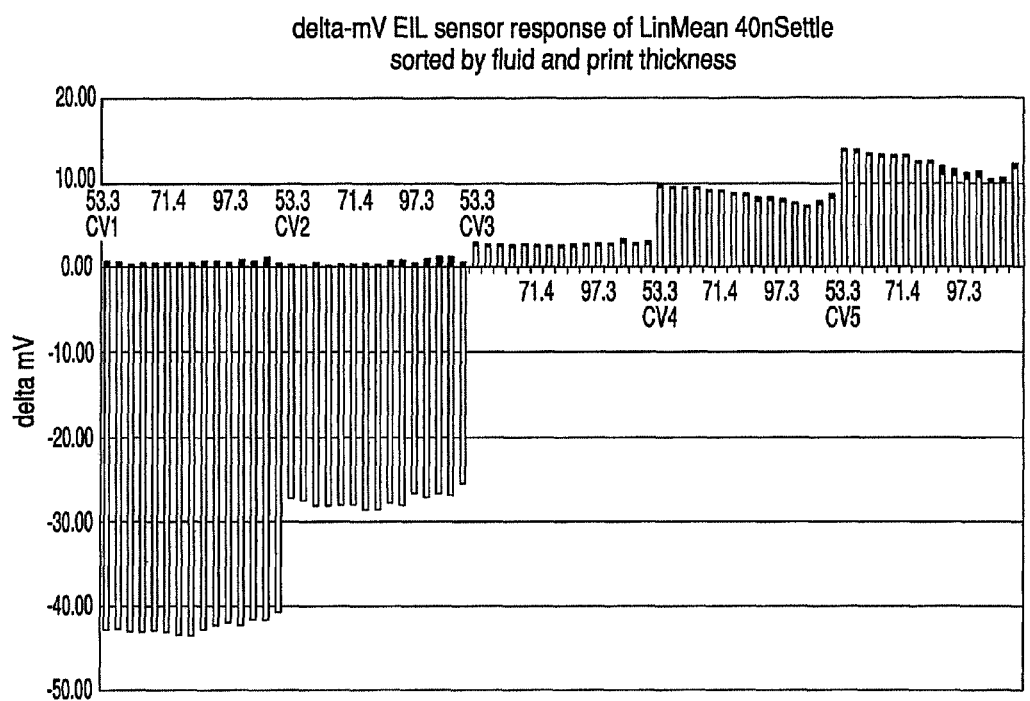
FIG. 18 demonstrates the relatively minor effect of print thickness of the EIL membrane on sensor performance using five different aqueous control fluids.

Importantly, with the EIL process, it was found that the impact of having consistently reproduced sensors is an increase in precision, reproducibility of print thickness, improved ease of manufacture and improved product yield. For example, FIG. 18 demonstrates that for a range of print thicknesses, the potential difference measured was not significantly impacted by print thickness, attesting to the robust nature of this EIL process. CV1, CV2, CV3, CV4 and CV5 are standard test fluids containing concentrations of urea at 152.5, 57.8, 10.7, 5.9 and 3.4 mg/dL BUN, respectively. In addition to urea, these solutions also contain other salts and buffering components. In FIG. 18, prints of thickness of 57.3, 71.4, 97.3 μm were tested and graphed.

When formulating an enzyme immobilization composition comprising one or more enzymes, an acrylic-based monomer, a water-soluble organic photo-initiator and a water-soluble acrylic-based cross-linker in a substantially homogeneous aqueous mixture, it is typically necessary to consider both solubility and buffering. Enzymes generally require an aqueous buffered solution near pH 7, but there are exceptions, e.g., alkaline phosphatase. Most photo-initiators also have limited solubility in aqueous based solvents. Additionally, acrylic resin cross-linkers are also only slightly soluble in aqueous solutions. The preferred 1-[4-(2-Hydroxyethoxy)-phenyl]-2-hydroxy-2-methyl-1-propane-1-one (manufactured by Ciba-Geigy, Irgacure 2959) when dissolved in the acrylic resin solution (monomer and cross-linker) was found to be slightly more soluble and could be dissolved into the aqueous solution. Higher concentrations of photo-initiator are preferred. It is important, however, that the photo-initiator does not precipitate out of solution and identifying an appropriate concentration range is important. Concentrations ranging from about 0.5 to about 4.0% (w/v) are preferred. As this photo-initiator is sensitive to UV light at 310 nm, it was found to be generally insensitive to indoor light, and was thus found to be useful for a production process without the need for red room or yellow room manufacturing conditions.

FIGS. 14(a) and (b) show a table of reagents for the spot curing matrix with preferred actual mixture compositions. The first example is for a spot cured sensor with the only enzyme being urease (FIG. 14(a)), and the second example is one for a urease and carbonic anhydrase combination (FIG. 14(b)). In the preferred urease mixture, the order of mixing is as follows:

Acrylic resins that are typically used for electrophoresis gels are at high monomer to cross-linker concentration compared to the acrylic resin formulations preferably employed in the present application. Electrophoresis type resins (e.g., acrylamide and bis-acrylamide) are typically at monomer and cross-linker concentrations of 0.2 and 0.007 g/ml, respectively, whereas the preferred matrix for the present invention has an acrylic resin formulation containing monomer and cross-linker concentrations of 0.05 and 0.02 g/ml, respectively. This higher cross-linker to monomer ratio is believed to be advantageous in reducing the physical change in the microdispensed print during curing and drying. In various embodiments, the composition includes a cross-linker to monomer weight ratio greater than about 0.04:1, e.g., greater than about 0.1:1 or greater than about 0.3:1. These ratios are also advantageous to sensor hydration with a biological sample (e.g., blood). To accomplish the desired monomer:cross-linker ratios and prevent precipitation out of solution, the typical gel electrophoresis cross-linker bis-acrylamide was replaced in the preferred embodiment with 1,4-bis(acryloyl)piperazine (BAP), which exhibits higher aqueous solubility.

Wafer Fabrication and Biosensors

Silicon wafers are preferably used as the solid substrate on which biosensor chips are created. Other materials e.g., plastics alumina and glass, can be substituted for silicon, however the Bonner is a convenient material for manufacture of planar structures at high volume, e.g., many millions of devices per year.

Onto the silicon, layers of materials are added at specific locations to create a set of individual chips. These processes are well known to those skilled in the art. For the present invention, a thin layer of silicon dioxide is preferably formed over the silicon by pyrolysis. Then titanium or a titanium-tungsten alloy is sputtered down and photoformed on top of the silicon dioxide layer. This is used as a layer for silver and other metals to adhere to. In this example silver and silver oxide are formed on the chip, as depicted in FIG. 2(a) using well known processes. In FIG. 2(a), the contact pads 350 for connecting to the analyzer device are connected to the various sensors and electrical connectors. Specifically, the underlying layer of the BUN sensor 353 contains silver and silver chloride. The chloride sensor 352 also has a silver/silver chloride layer. The ground electrode 351 is a photoformed silver chloride electrode with multiple contact points with the sample. It forms the ground potential for electrical measurements of other sensors on the chip. The reference electrode structure is depicted by 354 and described in detail in U.S. Pat. No. 4,933,048 and Published U.S. Appl. No. 20070015977, the entireties of which are incorporated herein by reference. These layers preferably use several photo-definable masks in their process to permit accurate deposition of materials at specific locations.

FIG. 2(b) depicts a next step in the process wherein the ammonium ionophore layer 355 is deposited on top of the BUN silver/silver chloride deposition shown in FIG. 2(a). The ammonium ionophore layer and methods for its preparation are described in U.S. Pat. No. 5,200,051, the entirety of which is incorporated herein by reference. This is followed by microdispensing the chloride (CL) sensor 352, shown in FIG. 2(c), along with the UV based BUN EIL membrane 356 of the composition described in FIG. 14.

FIG. 1 depicts in a topological manner the cross sectional layers of a BUN sensor according to one non-limiting embodiment of the present invention. The BUN sensor shown includes reference sensors described in the process reflected by FIGS. 2(a)-(c). The silicon wafer 320 is covered with a silicon dioxide layer 315, along with titanium or titanium-tungsten alloy 310, followed by silver 305 and silver chloride 304. A PVC ionophore composition 325 is printed above the silver/silver chloride layer, followed by the EIL enzyme layer 311 containing the urease enzyme.

In FIG. 1, the reference electrode also contains all the above described layers found up to the silver/silver chloride layer 304, but also contains an electrolyte layer 312, a gas permeable membrane 308 and optionally is processed with a photoresist cap 309.

Automated Integrated Microdispensing and Spot Curing System

In a preferred aspect of the invention, the microfabricating process of the invention is an automated system, which is able to microdispense precise and programmable amounts of the materials in select regions of a planar surface material used in the sensors of interest and additionally provide for integrated curing, preferably spot-curing, by means of UV radiation. The key concept in this aspect is controlling the time domain with regard to the microdispensing step and the timing and duration of the subsequent UV exposure step. Here, control of the time domain is typically in fractions of seconds. This is consistent with high volume manufacturing processes familiar for microfabricated devices.

In one embodiment, the dispensing head comprises a syringe needle with a reservoir for the matrix, and a displacement means for controlling the dispensed volume from the syringe and onto the selected surface. The apparatus also includes a step and repeat mechanism for moving the surface, e.g., silicon wafer, with respect to both the dispensing head and said UV radiation source, thus enabling the formation of an array of immobilized enzyme layers at a set of pre-selected locations.

Preferably the controlled volume that is dispensed is in the range of from about 1 nL to about 10 µL, e.g., from about 5 nL to about 1 µL or from about 50 nL to about 0.1 µL, and the dispensed volume will cover an area in the range of about 10 square microns to about 75 square millimeters. Preferably, this area is substantially circular with radial dimensions in the range of from about 5 µm to about 5 mm.

In a preferred embodiment, the system provides a method of forming an organized array of immobilized layers on a substantially planar surface by dispensing a sequence of controlled volumes of a photoformable matrix, e.g., the above-described enzyme immobilization compositions of the present invention, at a pre-selected set of locations on a surface. This is followed by applying UV radiation beam onto an area substantially covering each of the pre-selected locations. Importantly, this occurs in sequence, starting at a predetermined time after each controlled volume has been dispensed and applying said radiation at a predetermined intensity for a predetermined duration, to form said immobilized array of immobilized layers. Preferably, the predetermined time is in the range of from about 0.1 to about 10 seconds, and the predetermined duration is in the range of from about 0.1 to about 10 seconds. Preferably, the method uses UV radiation in the wavelength range of from about 185 to about 400 nm and having an intensity in the range of from about 100 mW/cm$^2$ to about 10 W/cm$^2$. As is known by experts in the field, curing can be effected by generating a specific dosage of UV radiation at a selected site. It is well known that the parameters of time, intensity and distance all impact the UV radiation dose and can be adjusted to generate a specific UV dose. Typically, a high intensity can generate more heat and can have other effects on the process. The preferred method also uses a planar surface that is a silicon wafer and the pre-selected set of locations is an array of sensors on said wafer, typically based on unit cells in an X-Y array. In terms of the sequencing of the UV exposure after the printing step, the method preferably operates in a manner where the UV radiation beam is applied to the Nth minus X pre-selected location while dispensing occurs at the Nth pre-selected location. Typically, X is equal to an integer from 1 to 10. In the preferred embodiment for the urease membrane (311 and 356), the parameters UV exposure parameters include a 310 nm wavelength, 0.56 seconds of exposure to 4.2 W/cm$^2$ of radiation.

Figure 6:
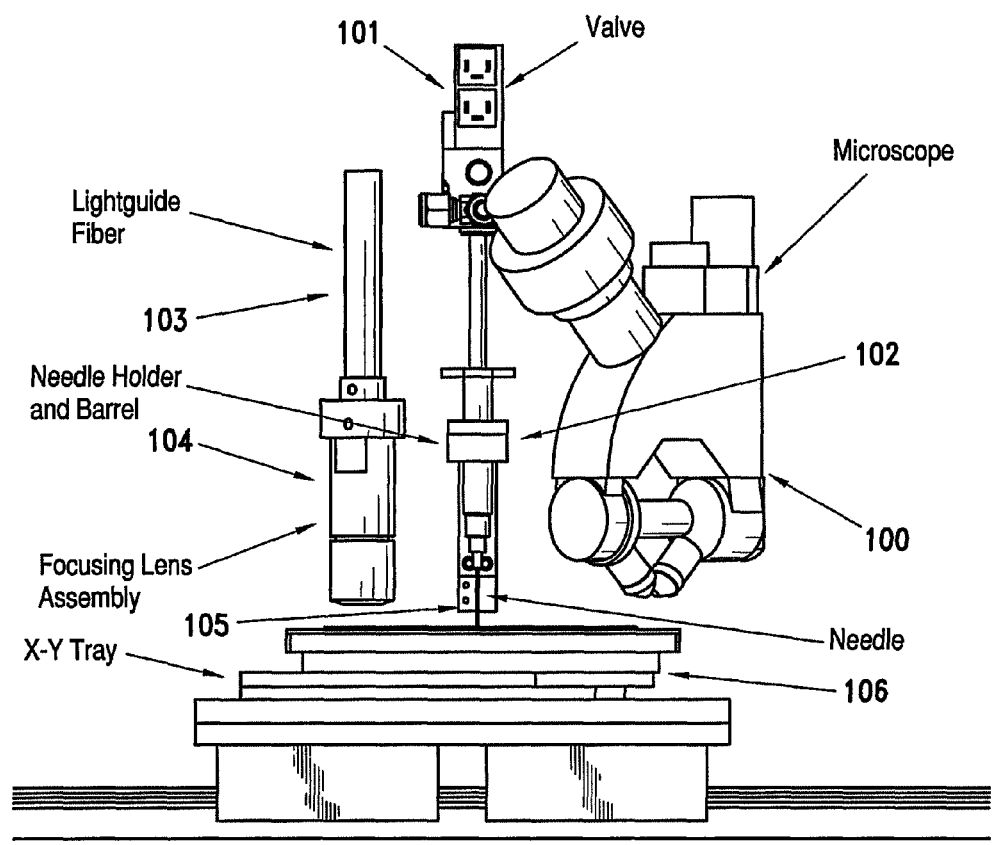
FIG. 6 shows a view of dispensing apparatus and UV spot-curing subsystem.

FIG. 6 illustrates a microdispensing system according to one embodiment of the present invention. As shown, the microdispensing system comprises a vacuum chuck 106 and a syringe 102 and 105, each of which are attached to separate means for altering one or more of the vertical, horizontal, lateral, or rotational displacement of these elements. For the sake of economy, it is sufficient to have means for changing the vertical displacement of the syringe so long as one can change the position of the vacuum chuck multi-directionally. The movements of both elements may be controlled via a personal computer. In one aspect, the position of the vacuum chuck may be reproducible within ±51 microns or better in either or both the x and/or y directions and the flatness of the chuck is within 1 micron.

The matrix formulations of the preferred embodiments of the present invention can be loaded into a microsyringe assembly 102 for the purpose of establishing layers in a controllable manner. The microsyringe assembly is preferably equipped with 25 to 30 gauge needles 105 having an internal diameter of 150 µm and an external diameter of 300 µm. Typically, the microsyringe needle 105, which includes an elongated member and a needle tip, is made of a metallic material, such as, for example, stainless steel. Additional layers may be coated onto the needle to change its surface properties. Furthermore, other materials such as synthetic polymers may also be employed in manufacturing the main body of the needle, itself. Depending on the pretreatment of the electrode surface and the volume amount of fluid applied, membrane layers of a thickness ranging from about 1 to about 200 µm can be obtained consistently.

The UV cure microdispensing subsystem (FIG. 6) optionally comprises a valve 101 connected to tubing which connects to the needle holder and barrel 102, as well as the needle 105. The microdispensed drops can be optically monitored using a microscope 100. The microdispensed drops are cured using the UV light from the focusing lens assembly 104 using radiation from optional light-guide fiber 103.

Figure 7:
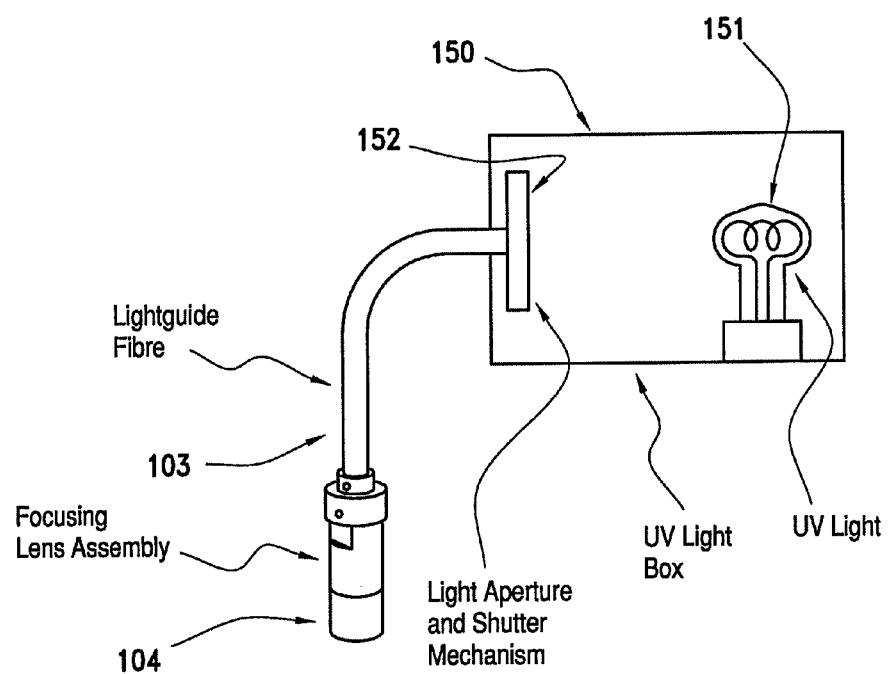
FIG. 7 shows details of the spot-curing subsystem and the UV light box.

Non-limiting FIG. 7 shows the radiation focused in focusing lens assembly 104 using radiation from the light-guide fiber 103, which radiation is generated by a UV bulb 151 in the UV light box 150. As shown, the amount of light radiation and the time of exposure is controlled using a shutter/aperture 152 in the light box 150. The latter is optionally performed with an algorithm in a computer.

Figure 8A:
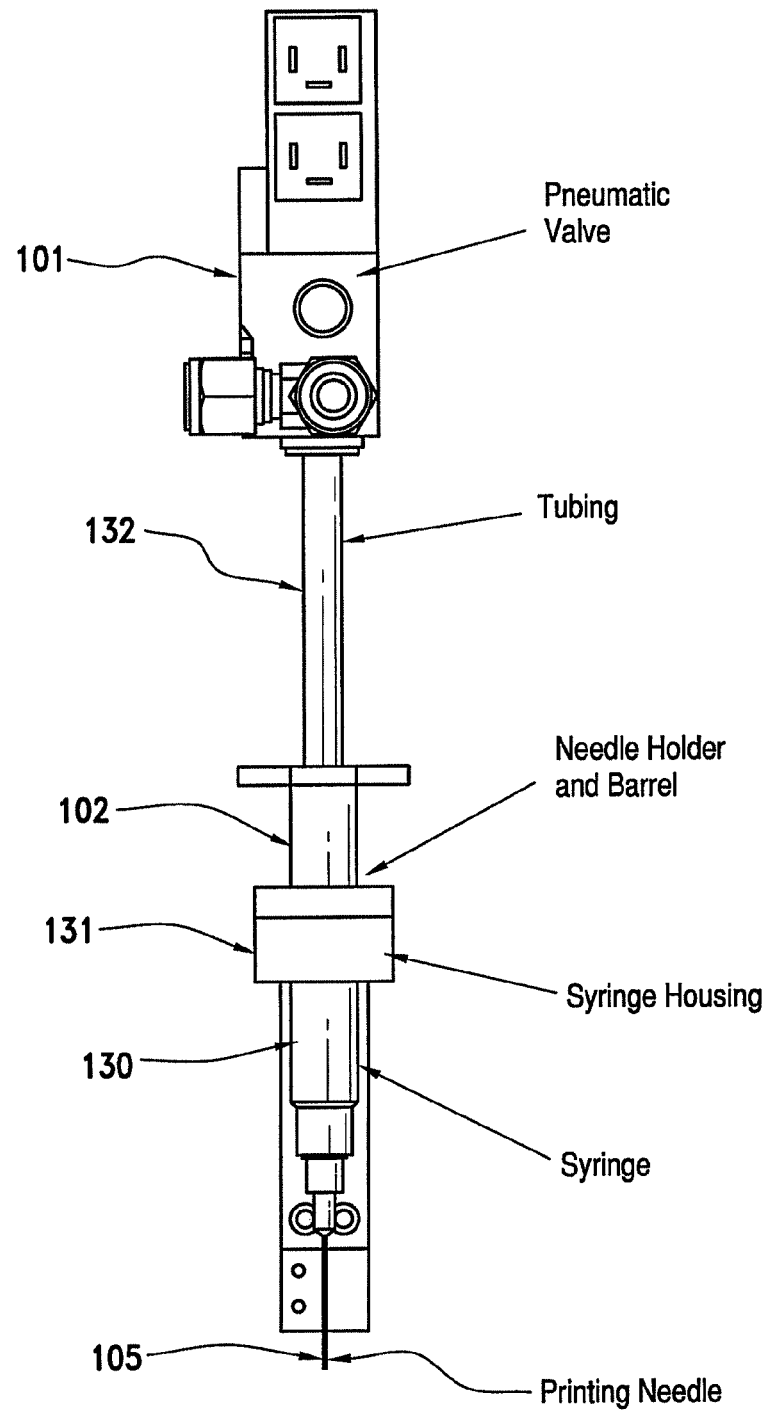
FIGS. 8(a)-(b) shows details of (a) the dispensing and (b) the spot-curing subsystems.
Figure 8B:
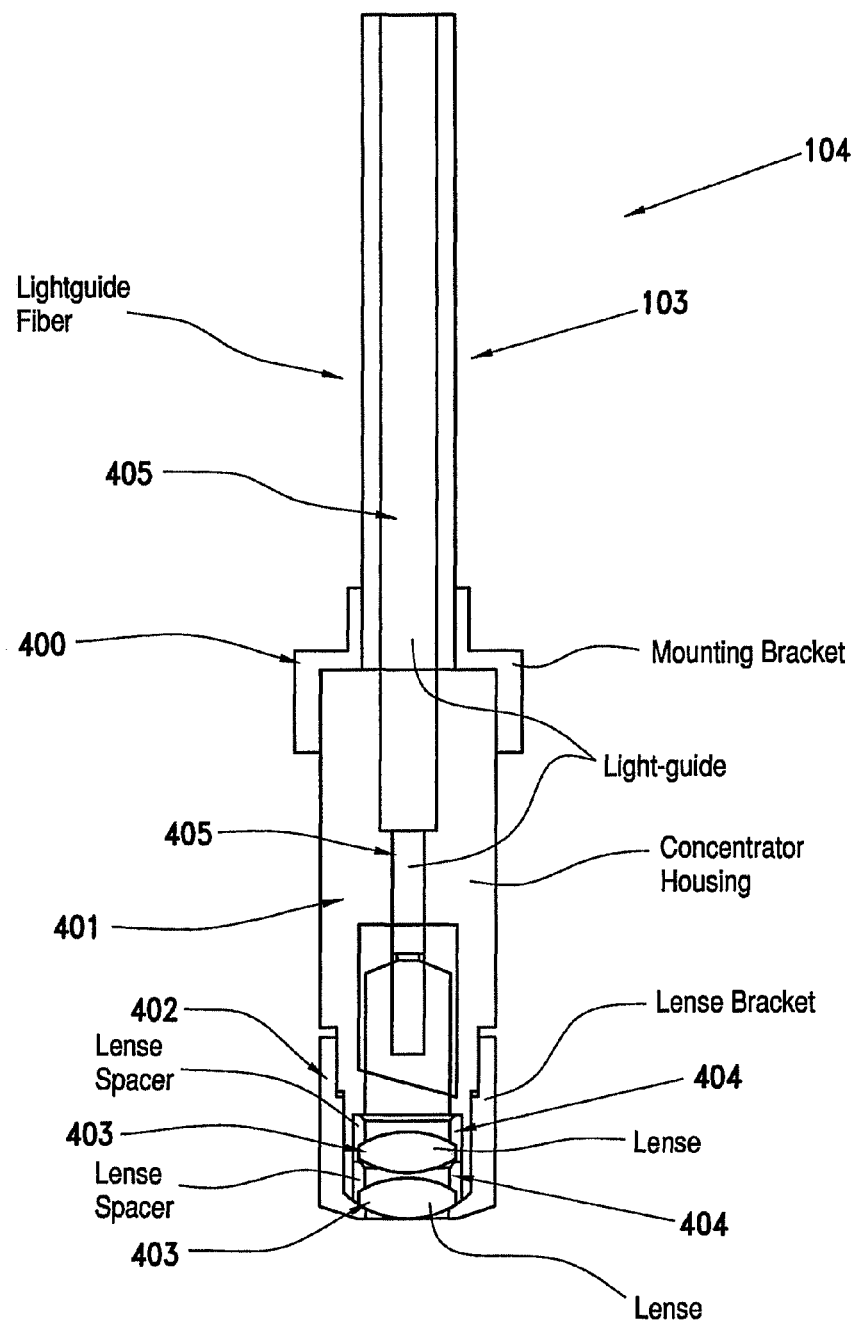

One non-limiting embodiment of the microdispense system is further illustrated in FIG. 8(*a*) where the pneumatic valve 101 generates pressure for the system along tubing 132 into the needle holder and barrel 102. As shown, needle holding and barrel 102 is held by syringe housing 131, which holds syringe 130. Syringe 130 allows the delivery of microdispensed drops through needle 105.

An optional embodiment of the UV focusing lens assembly 104 is further illustrated in FIG. 8(*b*) wherein the UV light is provided to the concentrator housing 401 via light-guide fiber 103 through light-guide 405. The concentrator housing 401 is attached to light-guide fiber 103 using a mounting bracket 400. The light is focused in this example with two lenses 403 held in place with a lense spacer 404 in the lense bracket 402. One lense might be sufficient, but additional optional lenses are optional, and understood by those skilled in the art.

Figure 9:
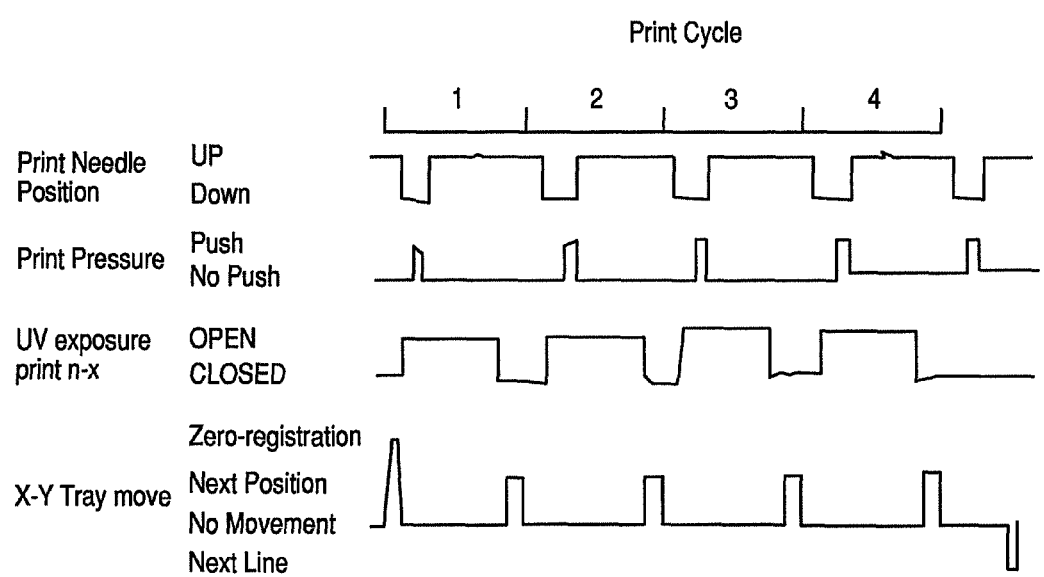
FIG. 9 shows process algorithm steps and timing for dispensing and spot-curing.

The optionally computer controlled process for the microdispensing and UV curing may be run by an algorithm depicted in FIG. 9 wherein the needle is moved up and away from the X-Y tray which in turn is placed into the first print position. The needle is moved down into close proximity to the printing location, followed by print pressure being generated for a brief time period. The needle is then raised after the print pressure has finished dispensing a droplet. Concurrently with the microdispensing process, the trailing UV cure process is started once the X-Y tray has positioned itself to a new print location and finishes prior to it moving again. This process is repeated for each print location until all positions are printed and cured.

The drop sizes that can be dispensed reproducibly extend over a wide range. For volume sizes between about 5 to about 500 nanoliters (nL), the drops can be applied preferably with a precision of about 5%. A solenoid having a 0.1% precision rating is sufficient for this purpose. The height of the tip of the syringe needle above the sensor preferably is between about 0.1 to about 1 mm, depending on the volume to be dispensed. Generally, the smaller the volume of the drop, the lower the elevation of the needle from the sensor. The precise alignment of the syringe needle with the preselected area of the sensor can be achieved optically by means of a camera and a reticle. Such an operation can be performed manually by an operator or automatically by means of a visual recognition system. The latter is preferred.

It is useful to consider the dynamics involved when a single drop of fluid is formed and expelled from a needle. As more fluid is expelled from the needle tip, the drop will grow in size until the gravitational force acting on the mass of the drop exceeds the opposing forces maintaining contact with the needle tip. These opposing forces include the adhesive forces between the needle tip and the fluid or liquid, and surface tension of the liquid itself. It is well established that at low liquid flow rates where discrete drop formation is complete, the drop volume is fixed. However, the volume may be changed by varying any of the fluid related parameters discussed above, or by changing the diameter of the needle tip thus changing the available surface area for fluid adhesion. For example, a hydrophobic polytetrafluoroethylene (PTFE) coating applied to the needle tip reduces the natural drop size of an aqueous based matrix material by reducing the adhesive forces between the drop and the needle tip. In circumstances where a controlled volume must be microdispensed onto a surface, it is possible to have the microsyringe tip positioned above the planar surface at a height which does not allow the drop to form completely (and then fall to the surface under the influence of gravity), but the partially formed drop actually contacts the surface and the new adhesive forces between the liquid and the surface begin to spread the drop. If the needle tip is now retracted in the Z-direction a sufficient distance away from the surface, then the cohesive forces of the liquid is overcome and a volume of liquid less than the fixed drop size will remain in contact with the surface. This technique can be used to dispense reproducibly any volume of liquid from about one-one thousandth of the fixed drop size and greater.

The surface tension between a pure liquid and its vapor phase can be changed by adding reagents. For example, a fatty acid added to water reduces the surface tension, whereas added salts can increase surface tension. The micro dispensable fluid compositions of the present invention preferably are prepared to have a controlled optimized surface tension. Suitable additives may be used when necessary. The hydrophobicity or hydrophilicity of the fluid is controlled in the same manner. Where a cured membrane is required as the end product, the solids content and volatile solvents content preferably are carefully adjusted. Moreover, the ratio of these components is also used to control the viscosity.

The preferred microdispensable compositions for the ammonium ion sensor comprises PVC polymer, plasticizers, ionophores and solvents with viscosities generally higher than those used for planar casting (e.g., spin-coating) of membranes. These higher viscosity compositions cure or dry without deformation of the membrane layer. Related problems, e.g., that of ensuring the homogeneity of the matrix at high viscosity and thus preventing phase separation of materials after time (i.e., considerations related to shelf-life) are also alleviated by these compositions. Other additives are also used to prevent long-term degradation of the membranes.

In addition to the factors described above relating to controlled volumetric dispensing of fluids having an optimized surface tension associated with a prescribed composition, tailoring the surface free energy of the substrate, or surface onto which the fluid is dispensed, provides control over the final dimensions, especially the thickness, of the resulting layer. The resulting process is highly versatile, allowing the deposition of arrays of layers of varied composition and utility. For establishing thick membranes, (e.g., 40-60 µm thick), the surface is preferably tailored so that the contact angle which the microdispensed fluid makes with the surface is large. For example, before an aqueous based enzyme matrix is microdispensed, the surface may be first plasma treated to give a controlled contact angle. For the preferred urease matrix, a carbon tetrafluoride plasma step yields a contact angle in the range 50°-70°.

An improved aspect of the microdispensing system, described here, is the integration of an automatic spot curing component. An EXFO Omnicure UV system is preferred for integration due to its ability to continually monitor and adjust the light aperture to assure that the radiation intensity remained consistent throughout the process. This ameliorates the issue of a typical UV bulb intensity decreasing over its lifetime (~2000 working hours) by using 50% intensity as the set point. As there is a relationship between cure time and bulb intensity, a reasonably high setting is required to reduce the product processing time.

Another aspect of the UV cure process is the desire to focus the beam on the specific sensor to avoid UV exposure to other sensors. Focusing the beam needs to be appropriate to avoid being too limiting. This is because the visualization system used to align each sensor that is being processed needs enough flexibility to assure a robust process in the event that they are not accurately aligned. Intensity is related to the distance of the UV beam to the cure site, therefore, by being closer the intensity is increased and the product processing time is decreased.

While the invention is described primarily in terms of a silicon wafer with microfabricated ion-selective electrodes, other types of sensors can be fabricated to incorporate a surface onto which the disclosed composition can be dispensed or coated. These include optical sensors, fiber optic sensors, surface acoustic wave sensors, evanescent sensors, surface plasmon resonance sensors and optical wave guide sensors. It also includes various base sensors, e.g., electrodes, ion-selective electrodes, potentiometric electrodes, amperometric electrodes, conductimetric electrodes, enzyme electrodes, biosensors, optical sensors, fiber optic sensors, surface acoustic wave sensors, evanescent sensors, surface plasmon resonance sensors and optical wave guide sensors. Substantially planar surfaces for sensor fabrication can include silicon wafers, alumina wafers, liquid crystal substrates, glass substrates and plastic substrates and flexible plastic substrates. In preferred embodiments, membrane-forming compositions are exposed to sufficient UV radiation to cause significant cross-linking, thus forming an adhered non-swelling immobilized enzyme layer on the surface.

The integrated microdispense and UV cure device is preferably automatically programmed in order to optimize the manufacturing process time and to effect UV curing. The microdispensing and UV curing steps preferably are run in tandem. In a preferred aspect, the UV curing step takes approximately 0.5 seconds, whereas the microdispense step takes about 0.3 to 0.4 seconds. Therefore, the microdispense step is typically rate limited by the indexing time of approximately 0.1 seconds between print sites. The microdispense and the UV cure subsystems preferably operate at two different, but adjacent physical locations during the same time period, wherein the microdispense step occurs before and ahead of the UV cure operation. FIG. 9 provides a preferred algorithm for operation.

The dispensing apparatus with the integrated UV radiation source preferably has a registration and alignment means capable of focusing a beam of radiation onto an area substantially covering the location at which a drop of matrix has been dispensed. A computer means is able to switch the UV radiation on and off, and this occurs at a predetermined time and for a predetermined duration (and also at a predetermined intensity), after the matrix has been dispensed. The registration and alignment means permits a beam to be focused on a selected area of said surface and illuminate an area in the range of about 10 square microns to about 75 square millimeters.

Each wafer preferably is manufactured with a plurality of chips (typically about one thousand on a 5 inch wafer), each containing one or more sensors and in this case each containing the BUN sensor. These sensors are desirably arranged in a uniform X-Y arrangement on the wafer. For processing of the wafers in the preferred embodiment, the chips are preferably generated by first placing an adhesive tape on the back of the wafer followed by cutting the wafer into individual chips using, for example, a diamond dicing saw. This process causes a slight displacement and uneven arrangement compared to the original location of the chip on the wafer. To compensate for this, a microscope 100, as depicted in FIG. 6, is used along with visual recognition software to realign the chip for the microdispense process. For the initial alignment and registration of the UV cure system, a UV sensitive paper is used to determine the proper alignment. Alternatively, a visible light source can be inserted in place of the UV light source 151 above the light guide 103 in order to align and focus the UV cure site. Yet another alternative approach would be use a UV monitoring device (radiometer) which has a focusing point and the intensity and activity is used to align and focus the UV cure site. Note that alternatively the dicing step can be performed after dispensing and spot-curing, however care is required to ensure that the water coolant used for the dicing blade does not result in dicing dust damaging the cured membranes. Where the substrate is plastic rather than a silicon wafer, dicing is by a simpler cutting process where dust damage is not an issue. Here dicing after dispensing and spot-curing is preferred.

Cartridge Construction for the Use of Improved Sensors

The diced silicon chips described above are then preferably used as subcomponents for disposable plastic cartridges. Each cartridge typically contains several features allowing it to process a patient sample with an analyzer device and determine the presence or amount of an analyte, e.g., urea, in the sample.

Figure 10:
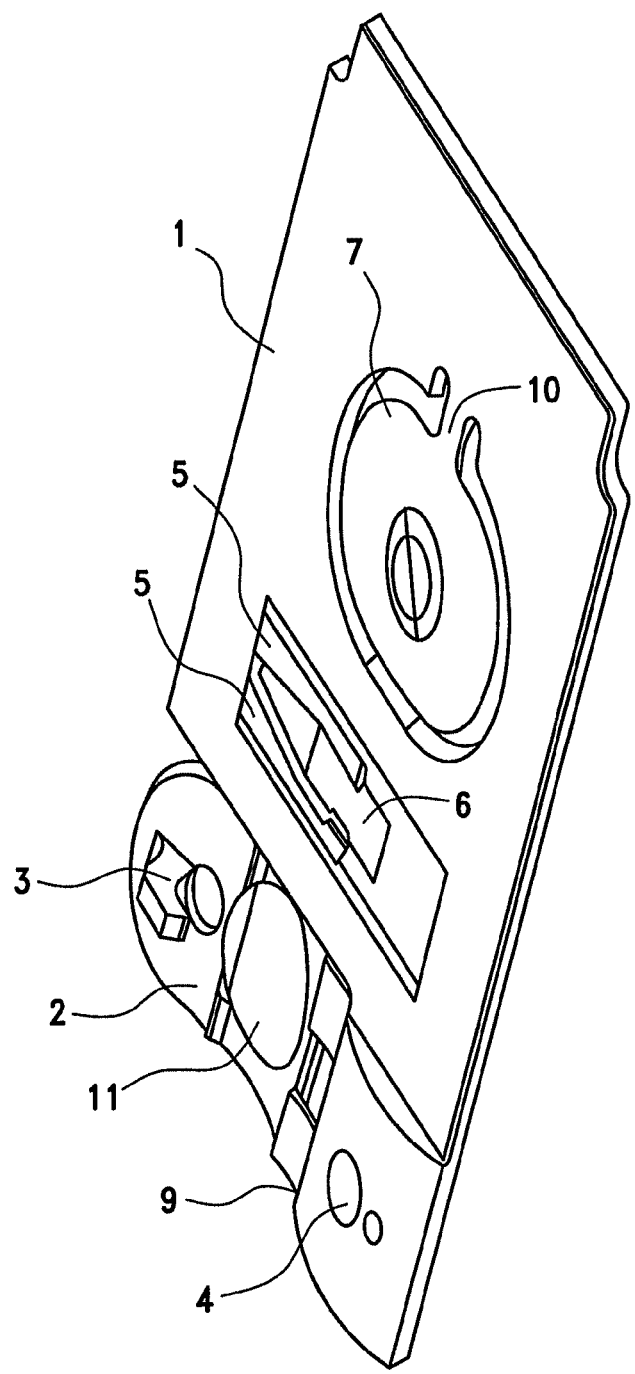
FIG. 10 is an isometric top view of a sensor cartridge cover.
Figure 11:
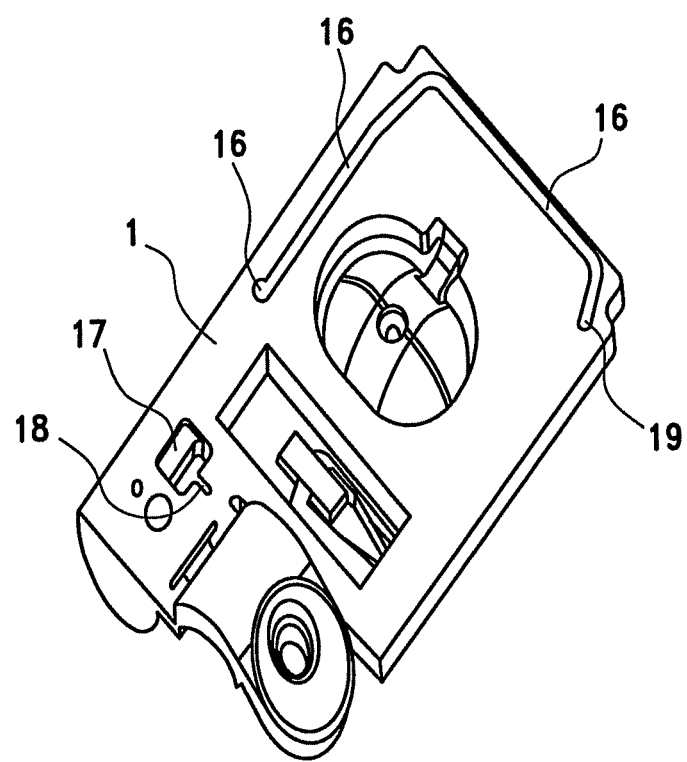
FIG. 11 is an isometric bottom view of a sensor cartridge cover.
Figure 12:
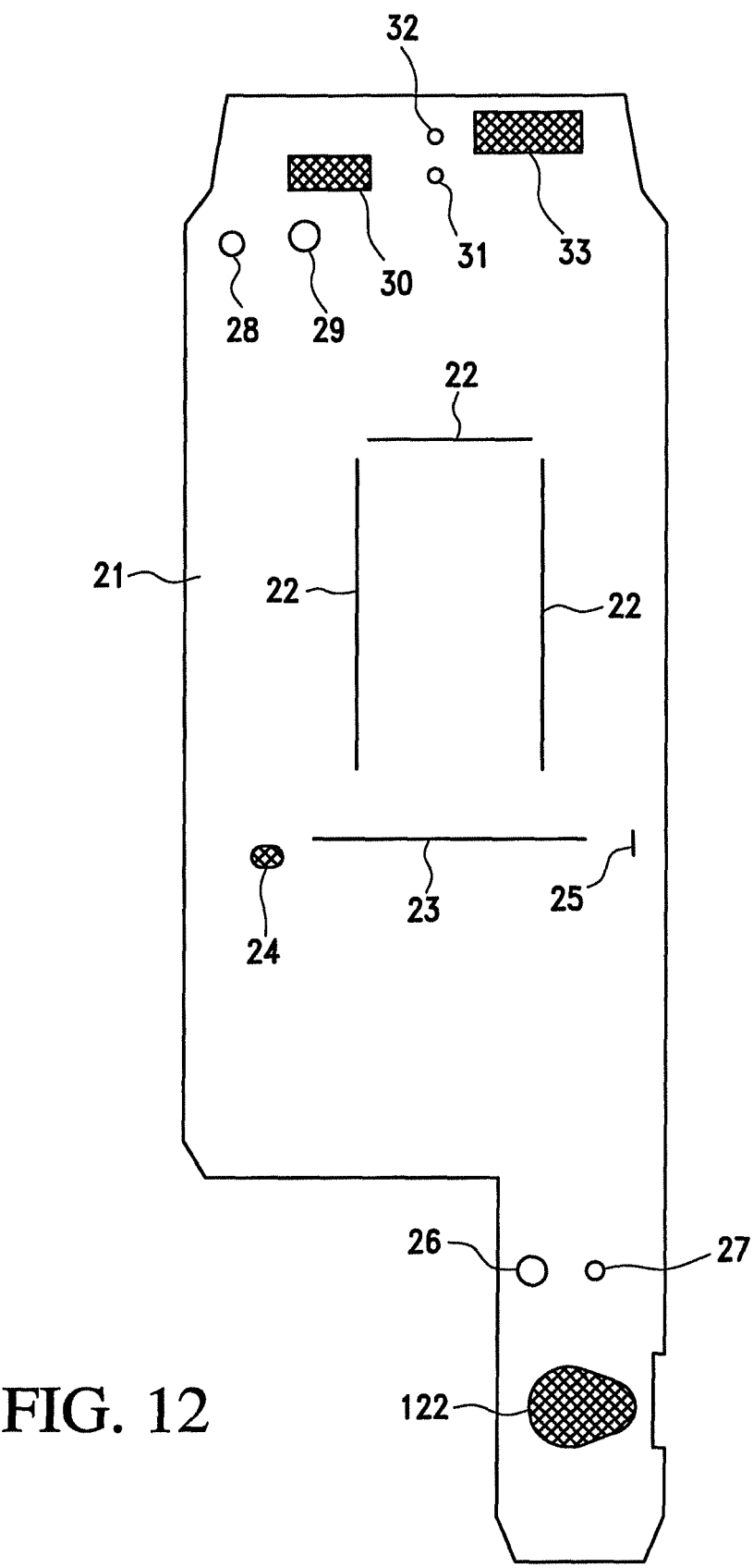
FIG. 12 is a top view of the layout of a tape gasket for a sensor cartridge.
Figure 13:
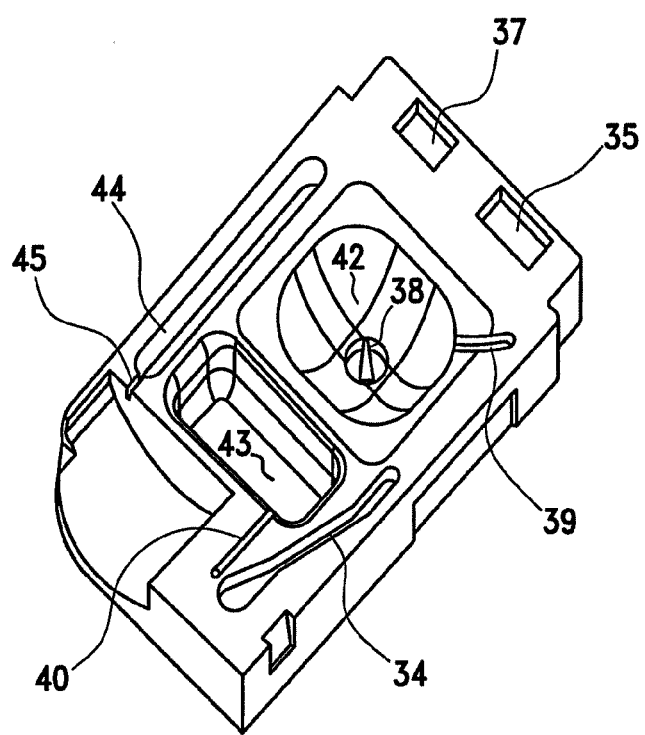
FIG. 13 is an isometric top view of a sensor cartridge base.

Referring to the figures, the cartridge for accepting chips of the present invention comprises a cover (two views), FIGS. 10, 11, a base, FIG. 13, and a thin-film adhesive gasket, FIG. 12, disposed between the base and the cover and securing them together. Specifically, the backside of the cover shown in FIG. 10 mates with the exposed face of the gasket of FIG. 12, and the backside of the gasket mates with the exposed face of the base of FIG. 13. Referring now to FIG. 10, the cover 1 is made of a rigid material, preferably plastic, and capable of repetitive deformation at flexible hinge regions 5, 9, 10 without cracking. The cover comprises a lid 2, attached to the main body of the cover by a flexible hinge 9. In operation, after introduction of a sample into the sample holding chamber 34, the lid can be secured over the entrance to the sample entry port 4, preventing sample leakage by means of deformable seal 11, and the lid is held in place by hook 3. The cover further comprises two paddles 6, 7, that are moveable relative to the body of the cover, and which are attached to it by flexible hinge regions 5, 10. In operation, when operated upon by a pump means, paddle 6 exerts a force upon an air bladder comprised of cavity 43, which is covered by thin-film gasket 21, to displace fluids within conduits of the cartridge. When operated by a second pump means, paddle 7 exerts a force upon the gasket 21, which can deform. The cartridge is adapted for insertion into a reading apparatus, and therefore has a plurality of mechanical and electrical connections for this purpose. It should also be apparent that manual operation of the cartridge is possible. Thus, after insertion of the cartridge into a reading apparatus, the reading apparatus transmits pressure onto a fluid-containing foil pack filled with approximately 130 μL of calibrant fluid located in cavity 42, rupturing the package upon spike 38, and expelling fluid into conduit 39, which is connected via a short transecting conduit in the base to the sensor conduit, 16. When the calibrant fluid contacts the sensors, they wet-up and establish a signal associated with the amount of calibrating ion or molecule in the fluid.

Referring to FIG. 12, thin-film gasket 21 comprises various holes and slits to facilitate transfer of fluid between conduits within the base and the cover, and to allow the gasket to deform under pressure where necessary. Holes 30 and 33 permit one or more urea sensors and one or more reference electrode that are housed within either cutaway 35 or 37, to contact fluid within conduit 16.

Referring to FIG. 13, conduit 34 is the sample holding chamber that connects the sample entry port 4 to first conduit 16 in the assembled cartridge. Cutaways 35 and 37 are locations in the housing for accepting the chips of the present invention. Optionally they also house a conductimetric sensor for determining the position of air-liquid boundaries. Recess 42 houses a fluid-containing package, e.g., a rupturable pouch, in the assembled cartridge that is pierced by spike 38 because of pressure exerted upon paddle 7 upon insertion into a reading apparatus. Fluid from the pierced package flows into the second conduit at 39 and then into conduit 16. An air bladder is comprised of recess 43 which is sealed on its upper surface by gasket 21. The air bladder is one embodiment of a pump means, and is actuated by pressure applied to paddle 6 which displaces air in conduit 40 and thereby displaces the sample from sample chamber 34 into conduit 16.

Improved Method of Forming and Curing Membranes Arrays

In one embodiment, the method of manufacture of a BUN sensor requires two separate printing events. The first step involves an $NH_4^+$ ion-selective electrode (ISE) print step followed by a urease layer print step. As described above, the printing process preferably uses a pneumatic pump and valve with a fine gauge needle on top of an X-Y table to accurately microdispense a drop onto a specific location on a wafer. Several controllable factors contribute to overall sensor performance. These include: (i) accurate registration of the printed drop over the desired location, (ii) the appropriate viscosity and surface tension of the drop, (iii) the associated hydrophobicity of the surface, (iv) the height and width (or volume) of the drop, (v) the height of the drop after drying on the surface, and (vi) good adhesion. Furthermore, the formation of crystals (partitioning) or cracking of the dried droplet can adversely affect sensor performance.

The prior art enzyme membrane (see, e.g., U.S. Pat. No. 5,200,051) is composed of a film-forming latex, preferably ELVACE (Forbo Adhesives Synthetic Polymers, Morris, Illinois).

However, this heterogeneous material can be susceptible to drying and blocking the microdispensing needle tip which can have an adverse affect on manufacturing. The surface tension of the ELVACE can also create irregular shaped structures which may impact the performance of the sensor. See FIG. 3(a). Additionally, ELVACE, which is a vinyl acetate ethylene (VAE) copolymer composed of hydrophilic and hydrophobic domains, can degrade over time, most likely generating acetate which makes the material more acidic. This time dependent process reduces the usable lifetime of the material. As a result, it is desirable to replace this heterogeneous matrix with a substantially more stable composition, preferably a homogeneous aqueous matrix which can be photoformed and provides a stable immobilization environment for enzymes, e.g., urease.

The present invention solves several lifetime issues including: the lifetime of the raw materials, the lifetime of the aqueous matrix prior to print, and the lifetime of the printed and cured matrix in the completed sensor. It also survives contacting a blood sample in the final product without dissolving away. This provides evidence of good adhesion characteristics that are highly desirable for reliable sensor performance.

Most importantly for a reliable manufacturing method, the present invention provides a microdispensable matrix that remains in solution at storage temperatures in the range of about 4° C. to about 35° C. without precipitation of the sub-components. It can also be stored frozen and melted for use without deleterious effect. Advantageously, the matrix composition also has adequate UV transmission, printed at thicknesses in a range extending to about at least 200 μm, to have a high degree of polymer conversion throughout the matrix.

The present invention is advantageous as the matrix exists in a state of low viscosity during the printing process, and then is controllably converted by UV radiation into a gelled or fixed state. This controlled approach using a UV cure process requires the incorporation of a UV photo-initiator in the formulation. This also requires a curing system that can generate controlled UV radiation directed to the part being cured. This specification of this UV curing system needs to provide for (i) simple automation, (ii) operation on a short cycle time compatible with the printing system, (iii) avoiding racking diced wafers during the curing process, (iv) avoiding the need for an oven or heat curing step, and (v) avoiding the need for continuous matrix mixing. In addition, it is desirable to avoid unnecessary material wastage. As previously mentioned, from a manufacturing perspective it is also useful if a large batch of material is made, pre-aliquoted and stored in frozen form.

The present invention permits a robust manufacturing process. The aspects of a robust manufacturing process permit some range of precision at each step in the process while generating a consistent product result. For one step in the process, the print thickness can vary slightly. From data (see FIG. 18), the mean potentiometric signal was advantageously found to be independent of the thickness of the print. Further, the standard deviation of these values across a lot of wafers is fairly independent of print thickness. This allows a wide range of enzyme layer thicknesses without impacting product performance.

Various UV systems may be used including a light wand, UV flood cure with or without an oven step, and a light-guide system. A UV laser can also be used for this process to deliver a focused beam of radiation to the printed sensor site. For the process of curing printed membranes on a silicon wafer or similar substrate, e.g., glass and plastic, a light wand is required to be positioned over every print location. This can increase the cure step time by n x t, where n is the number of chips/print locations and t is the time in seconds of each UV cure step. In one embodiment, a UV cure step is provided by a system accurately moving a light wand to each successive print location. The light wand movement is integrated with the print event at each print location.

For a system where the UV source moves independent of the print head, the matrix is first printed at a specific location by the print needle. The print needle moves away from the surface, preferably in the Z direction. The UV source then moves into location, followed by a UV cure exposure at the print location.

In a system where the UV source trails by a fixed off-set from the print site, the print needle prints in the fashion of a typewriter style print process (e.g., from left to right, followed by a return to the left side and an index to the next line of print sites, which are again processed from left to right). A UV source is located one or more print sites away, n, from the print needle location. The print needle prints the first print site, and then another print site until it reaches n print sites. Trailing along behind the print needle is the UV source. Once the UV source is located at the first print site on the left, n sites away from the print needle, the UV source exposes and cures the print site. As the print needle moves to the next print site, the UV source moves to the next site and while the print needle dispenses the matrix, the UV source exposes the print site. This print and trailing UV cure process continues until the print needle reaches the right side of the planar surface. In order to finish the UV cure process, the needle continues to move to the right with the associated movement of the UV source which continues to cure the remaining n sites. The print needle may be programmed to stop printing for the remaining print sites. The print needle and UV source are indexed to the next row to be printed and the setup begins at the left side of the planar surface. It should be understood by those skilled in the art that the print needle and UV source could be fixed in their position, and the table holding the planar surface moved to effect the movement of the print needle and UV source to each individual print site. Those skilled in the art will recognize that other engineered registration means can be used to accomplish the objective of ensuring consistent control of the time domain, such that each dispensed layer is cured at a fixed time and in a fixed manner after it is printed.

In the preferred embodiment a light-guide is used. The light-guide is effectively a conduit for light where the light is to be focused onto a small region of a wafer and where it is not delivered in a straight line from the UV source. The UV radiation is directed along the light-guide by a light fiber connection. This has the advantage of a light wand system where the lamp and filters are contained in the power box and the "flashlight" uses a very small footprint at the location of the cure site. Additionally, the UV radiation contains less attendant heat from infrared radiation and therefore keeps the cured part cool.

Where the particular photoinitiator present in the matrix requires specific radiation wavelengths, this is achieved by selection of specific UV bulbs appropriate for that specific photoinitiator. Most standard UV bulbs generate multiple wavelengths, some desired and some not necessarily desired. In applications with biological materials, it is preferred to have a specific radiation wavelength with no additional extraneous radiation at other wavelengths. Note that it is well known in the scientific literature that UVC radiation is less damaging biologically than UVA or UVB. Therefore, avoiding or limiting these wavelengths is preferable for biological samples. In the preferred matrix formulation which uses Irgacure 2959, the preferred radiation wavelength is about 310 nm. Common UV bulbs use mercury (type "H") and metal halide ("D"), which can both be used to cure as they generate UV A and UV B radiation required for the Irgacure 2959 photoinitiator containing matrix. However the "H" bulb has less extraneous radiation wavelengths and is preferred.

It is beneficial for the UV system to have an integrated optical filter allowing the passage of specific wavelengths of non-ionizing radiation, while preventing the transmittance of undesired wavelengths. In the preferred embodiment, radiation near 310 nm is required for the photoinitiator. As a means to limit the exposure of the sensor to deleterious wavelengths of radiation, a narrowband filter such as the Gilway and International Light Technologies, Inc. (Peabody, Mass.) Narrowband Filter NS313 which efficiently only permits wavelengths from about 300 to 340 nm is useful for preferred embodiments. Other filters used singly or in combination will be apparent to those skilled in the art to affect appropriate radiation wavelengths specific for certain other photoinitiators.

In a preferred embodiment, the light-guide system (FIGS. 6, 7 and 8b) has the advantages of spot curing with the capability to direct light to a specific location. In addition it can easily be filtered and does not generate the heat found in flood exposure based systems filtering Infrared (IR) radiation. It also does not require a separate shutter system, as this feature is already integrated into the device. This approach is also desirable for integration with the microdispensing system, as the power supply can be positioned outside of the microdispense housing with only the light-guide and concentrator housing with its associated lenses inserted inside the microdispensing unit minimizing footprint.

It is desirable that the UV-curable enzyme matrix has the following characteristics: (i) compatibility with enzymes and particularly for the preferred embodiment the enzyme urease enzyme, (ii) exhibit the appropriate flow and viscosity for good printing characteristics, (iii) compatibility with a reliable chemical formulation which can support a high-yield manufacturing process, e.g., incorporate an antimicrobial agent for improving matrix shelf-life and reagents for stabilizing an enzyme, (iv) be a water based technology to support biological reagents, (v) achieve reliable adhesion to a surface after UV curing step, (vi) provide for rapid wet-up when used in conjunction with a sensor, (vii) exhibit the appropriate enzyme substrate and water permeability when formed as a layer to support and sustain the enzyme reaction (viii) exhibit good electrical characteristics when used with an electrochemical sensor, and (ix) show an extended post-processing lifetime of greater than about 6 months at room temperature or under refrigeration, e.g., be compatible with genuine commercial product requirements. The compositions described in FIG. 14 have these desired characteristics.

The UV curing systems described herein can be used with each UV curable formulation to characterize many operating parameters including the precision and accuracy of the dimensions of cured membranes and adhesion of the membrane to the surface. The sensor can then be tested in cartridges to determine sensor performance with a given matrix and curing combination. This can include intra-wafer and inter-wafer variations, where each wafer may contain as many as a thousand sensors.

Figure 16:
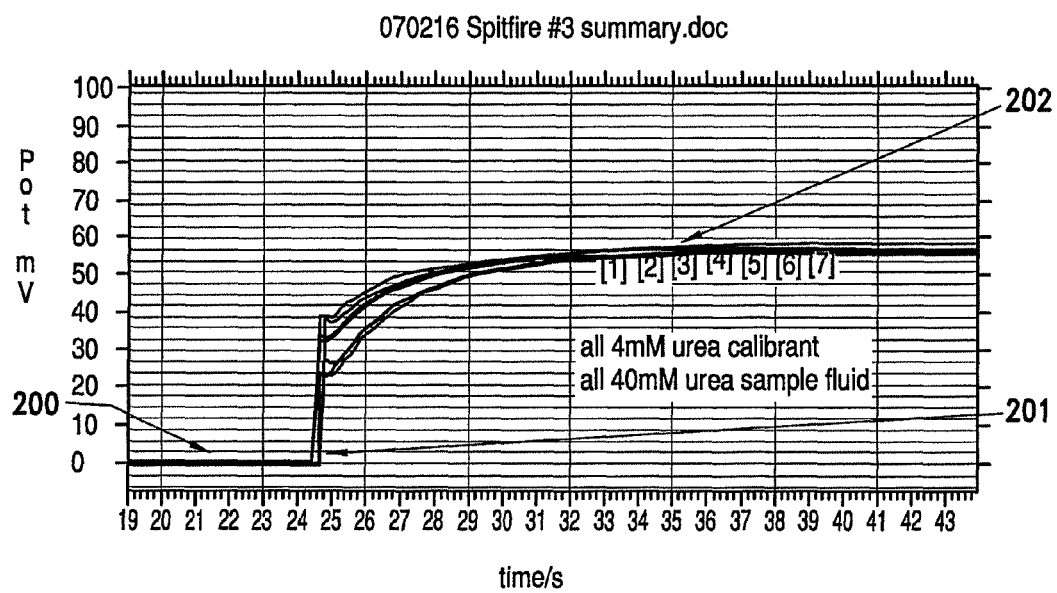
FIG. 16 shows chronopotentiometric data of signals generated from an acrylamide/1,4-bis(acryloyl)piperazine based enzyme immobilization layer after different intensity and times of exposure to UV light at 310 nm, demonstrating no significant impact of a range of time and intensity of exposures used in this experiment to UV light.

In FIG. 16 the effect of radiation on the sensor performance based on the matrix of FIG. 14(a). Batches of sensors were prepared using a flood lamp process and processes with 0.5 s, 1 s, 2 s and 3 s spot-cure UV radiation with radiation doses of 190, 380, 760 and 1140 mJ, respectively.

These data show that the processes are robust with various conditions of radiation giving acceptable test results.

Figure 15A:
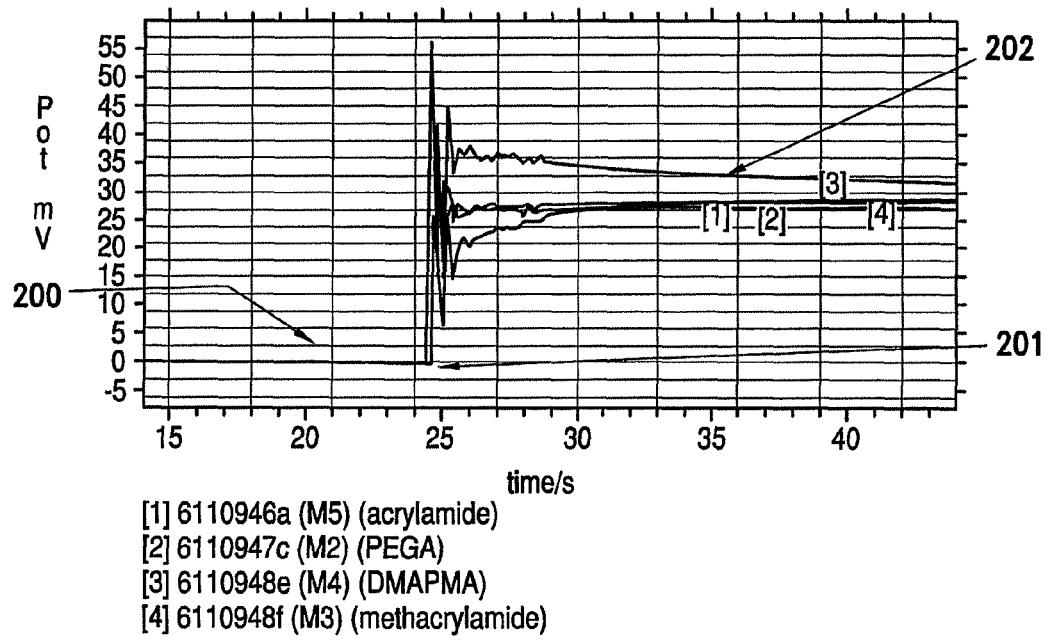
FIG. 15(a)-(b) shows chronopotentiometric data of signals generated from enzyme immobilization layers generated using (a) acrylamide, methyacrylamide, poly(ethylene glycol) acrylate (PEGA), and N[3-(dimethylamino)propyl]-methacrylamide (DMAPMA) as monomers and 1,4-bis(acryloyl)piperazine as dimer, (b) acrylamide as monomer and 1,4-bis(acryloyl)piperazine, polyethylene glycol diacrylate poly(ethylene glycol) diacrylate (PEGDA), N,N'-(1,2-dihydroxyethylene)bis-acrylamide (DHEBA) and trimethylolpropane ethoxylate triacrylate (TMPETA) as dimers.
Figure 15B:
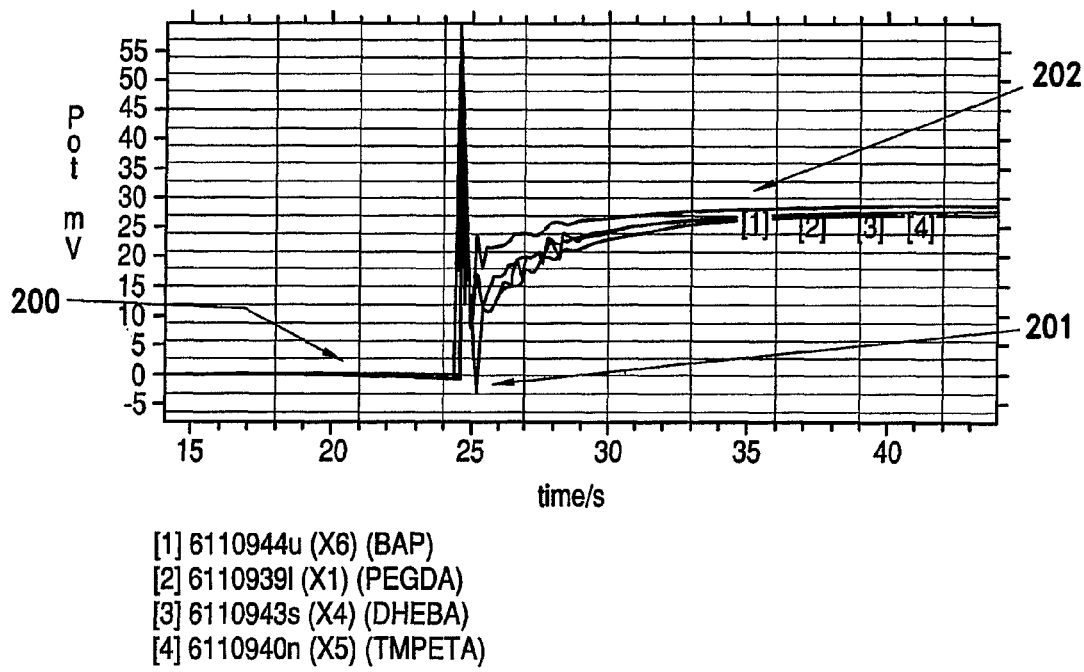

FIG. 15 demonstrates that compositions containing alternative monomers and crosslinkers generated similar sensor signals with test solutions. The monomers tested included acrylamide, methacrylamide, poly(ethylene glycol) acrylate (PEGA), and N-[3-(Dimethylamino)propyl]-methacrylamide (DMAPMA). Additionally, the crosslinkers tested included 1,4-bis(acryloyl)piperazine, polyethylene glycol diacrylate poly(ethylene glycol) diacrylate (PEGDA), N,N'-(1,2-dihydroxyethylene)bis-acrylamide (DHEBA) and trimethylolpropane ethoxylate triacrylate (TMPETA).

FIG. 17 shows an experiment where the absence of the humectant glycerol under accelerated lifetime storage conditions (e.g., 30° C. or 40° C.) had an affect on performance. By adding glycerol to the present matrix (see compositions in FIG. 14), a process with good performance and shelf-life is achieved.

Improved Blood Urea Nitrogen Sensor Manufacture

In one aspect, the intent of the present invention is to improve on the manufacture of BUN (blood urea nitrogen) sensors. The preferred embodiment of the new BUN sensor is manufactured using a combination of thin-film microfabrication processes and microdispensing techniques. It comprises a thin film silver-silver chloride indicator electrode operating in combination with a thin-film silver-silver chloride reference electrode of the type described in U.S. Pat. No. 4,933,048, incorporated by reference herein. A more preferable reference electrode is described in Published U.S. Appl. No. 20070015977, incorporated by reference herein.

In the initial step, a substrate wafer of silicon is overlaid with an insulating layer of silicon dioxide, by thermal oxidation. Metal layers of a titanium and tungsten alloy (TiW) and then silver are subsequently deposited onto the silicon dioxide base wafer and then patterned using photolithographic techniques. An electrically insulating layer such as polyimide polymer or additional silicon dioxide is then photo-patterned to isolate adjacent sensor circuitry. The silver-silver chloride indicator electrode (diameter ~200 microns) is prepared from the patterned silver using standard techniques, e.g., electrochemical, chlorine gas plasma and oxidation of $Ag^0$ by an inorganic oxidant such as $Cr_2O_7^{2-}$ or $Fe^{3+}$ in the presence of chloride ion.

The remaining layers of the BUN electrode include two thick-film structures: (i) a semi-permeable membrane film, comprising an organic polymer layer (e.g., poly(vinyl chloride)—PVC), and an ammonium ion ionophore; and (ii) the outermost biolayer, comprising in this particular sensor, a spot photo-cured acrylamide urease layer that optionally includes carbonic anhydrase. These layers are deposited by a microdispensing technique as described in U.S. Pat. No. 5,554,339, incorporated by reference herein. In the present invention, however, the microdispensing assembly described in the '339 Patent has been substantially improved to include an integrated ultra-violet spot-curing component system enabling automated printing and curing in a controlled time domain, as described above.

The thick-film ammonium ion-sensitive structure comprises a poly(vinyl chloride) (PVC) binder, tris(2-ethylhexyl) phosphate as a plasticizer, and nonactin as the ionophore. The indicator electrode can be made selective for different ions by using the same (or similar) binder and plasticizer composition but with different ionophores. For example, valinomycin, monensin and (methyl)monensin, and tridodecylammonium chloride have been used to make potassium, sodium, or chloride-ion selective electrodes, respectively. Other ionophores may include, but are not limited to crown ethers, trialkylamines, or phosphate esters, and the like. Alternatively, other polymeric binder materials may be used besides PVC. These polymers may include, for example, silicon rubber, polytetrafluoroethylene plastics, or derivatives of PVC containing ionizable functional groups (e.g., carboxylates). Other plasticizers suitable for use in the present invention may include, but are not limited to tris(2-ethylhexyl)phosphate, nitrocymene, 2-nitrophenyloctyl ether, dibutyl sebacate, diethyl adipate, phthalates, propylene carbonate, 5-phenylpentanol, or mixtures thereof. Still other binders and ionophore combinations may occur to those skilled in the art, which are within the scope of the present invention. The resulting semi-permeable ion-selective film may have a thickness in the range of about 2 microns to about 200 microns, preferably about 10 to about 30 microns. In the preferred embodiment, the ammonium ion-selective membrane solvent system is selected to provide the appropriate surface tension and stability. The solids content (wt %) of plasticizer, PVC polymer, and ionophore are preferably 60-80%, 15-40% and 0.5-3%, respectively. Various methods can be used to define a layer on a planar substrate. If a thick layer (about 5 to about 200 microns) is required, microdispensing of a viscous matrix, e.g., the photo-curable urease matrix described above, is generally preferred. Other methods for defining a layer on a planar substrate include, without limitation, spin-coating, dip-coating, spray coating, screen printing, ink-jet printing, laser printing, painting and contact printing are alternative methods and may be better suited to a different applications. For example, the preferred urease photoformable matrix may be screen printed onto a wafer in a single pass at a specific time (t=0). The screen optionally has an opening of 300 μm diameter, with each opening registered for alignment with an array of ammonium ion-selective membranes on the wafer. After the printing step a flood UV exposure of the wafer is performed at t=1. Similarly to the spot-curing method described above, this method also gives control of the time domain from printing to the UV step for each individual matrix. In this embodiment t=1 is preferably automatically set at 2-20 seconds after t=0. Automated equipment for moving wafers from a printing station to an exposure station is well known in the microfabrication art. The preferred urease matrix can also be spin-coated and photo-patterned with a mask, in the manner widely used in the microfabrication art.

Referring now to the topological illustration in FIG. 1, the substrate wafer, 320, is silicon, with an overlaid insulating layer of silicon dioxide, 315. In addition there is a polyimide layer 301 with two circumferential print wells (302, 303) which are used to confine the printed layers. The first metal layer, 310, is TiW and serves the functions of a conductor and an adhesion layer to the wafer. Succeeding layers 305 and 304, are the silver and silver chloride layers. On the left side of FIG. 1, the remaining layers of the indicator electrode include (i) a semi-permeable membrane film, 325, comprising an organic polymer layer (e.g., polyvinyl chloride (PVC)) and an ammonium ion ionophore; and (ii) the outermost biolayer, 311, comprising in this particular embodiment, an acrylamide photo-cured urease layer of the preferred composition described above.

The reference electrode portion of the unit cell may be comprised of overlaid structures as shown in FIG. 1. In this particular embodiment, the metal and chloridized layers of the reference electrode are covered by an electrolyte layer, which may comprise any material which is able to hold a high concentration of salt but which is, preferably, photoformable. In this respect, a polyvinyl alcohol (PVA) formulation is the preferred material and may first be photo-patterned and forms a water-permeable matrix that can subsequently be saturated with a salt, such as potassium chloride. A separate gas permeable membrane, may also be present which serves to diminish the loss of electrolyte or salt to the bulk analytical sample but allows the rapid wet-up (i.e., passage of water or other small gaseous molecules) of the reference electrode prior to commencing the sample analysis. The patterning process can be either of those described in U.S. Pat. No. 4,933,048 and Published U.S. Appl. No. 20070015977 both incorporated herein by reference. Alternatively, a reference electrode structure can be used in which the distance between the liquid junction and the surface of the silver/silver chloride is sufficiently large, such that the concentration of electrolyte in the immediate vicinity of the Ag/AgCl structure is substantially constant for a period of time sufficient to perform a measurement of the potential difference between the indicator electrode and the reference electrode.

Referring now to FIG. 2, indicator electrode and the adjacent reference electrode are each connected by an overpassivated signal line to a contact pad. The overpassivation (polyimide layer) includes print wells 302 and 303 formed as concentric circles. The unit cell is confined within a rectangular area, which is repeated in an array several hundred times on a single silicon wafer. In particular embodiments of the instant invention, other indicator electrodes may be present in the unit cell for the simultaneous measurement of other species (e.g., $Na^+$, $K^+$, $Cl^-$) in addition to ammonium ion.

To manufacture the BUN base sensor, a silicon wafer with a topical layer of silicon dioxide, which had previously been cleaned, scrupulously with a mixture of concentrated sulfuric acid and hydrogen peroxide is placed into a plasma deposition system and layers of TiW (0.1 μm) and silver (0.5 μm) are sputtered consecutively onto the wafer surface. The silver-titanium bilayer is then processed to localize it to a region, which in the final device acts as the ammonium ion sensor. This process is achieved by a standard lithographic technique in which the wafer is spin-coated with positive resist (Shipley AZ 1370 SF). After UV exposure of the photoresist through a mask and development (Shipley AZ 351), the exposed silver is removed by an aqueous solution of ferric nitrate (0.9 mM) as the etchant. The underlying titanium layer is then processed by means of the same photolithographic steps, but using an aqueous mixture of nitric acid (3.9M) and hydrofluoric acid (0.78 M) as the etchant. N-methylpyrrolidone solvent is then used to remove the remaining photoresist to expose the required silver structures (diameter about 150 μm).

To passivate the signal lines a photo-definable polyimide (DuPont 2703) is spin-coated onto the wafer. Once the wafer is UV exposed and developed with a solvent the polymer is baked in an oven at 350° C. for 30 minutes under an inert atmosphere and left to cool to 150° C. before removal. While the mask used for patterning defines the perimeter of the layer, it also defines print wells 302 and 303. These are subsequently used to control the dimensions of the two respective microdispensed membranes.

The silver is preferably then chloridized by dipping the entire wafer into an aqueous solution of potassium dichromate (12 mM) and hydrochloric acid (60 mM). The wafer is then washed and partially diced. Over these patterned silver chloride electrodes is placed an ammonium ion sensitive membrane. The membrane material is made by dissolving low molecular weight PVC (Sigma) and high molecular weight carboxylated PVC (Type Geon, Goodrich) (1:1 w/w) in a solvent system of cyclohexanone, propiophenone, and N-methylpyrrolidone (1:1:1 v/v/v) to a total solids content of 10 g/dL of solution. Dissolution is accomplished by heating the mixture at 70° C. for 30 minutes. To this mixture the plasticizer tris(2-ethylhexyl)phosphate (Fluka) is added, to provide a total solids content of 35 g/dL. The resulting mixture is then allowed to cool to 45° C. and nonactin (Fluka) is added in the amount equivalent to 2 percent of the total solids in the mixture. At room temperature, 10-100 nL of this final material is microdispensed onto each of the silver chloride indicator electrodes on the wafer, overlapping on all sides by at least about 30 μm. Print well 302 is preferably used to define the perimeter. Curing is accomplished by placing the wafer on a 60° C. hot-plate for 30 minutes. This process yields a stable, rugged structure having a thickness of about 15 μm.

In the final step the preferred urease matrix, described above, is microdispensed onto individual membranes and UV spot cured using the apparatus. Print well 303 is preferably used to define the perimeter. As mentioned above, in the preferred formulation the components are mixed together and frozen in a cryofreezer prior to use. This allows consistent production of product day-to-day and a long storage lifetime prior to microdispensing. This formulation can also be quality control (QC) tested prior to a microdispense event as the mixture can be assayed for enzymatic activity using a standard reference method using a spectrophotometer. This reduces the cost and waste in making product in the manufacturing process.

Regarding the preferred standard assay method, the urease enzyme activity from an aliquot of the thawed frozen formulation is assessed using a modification of the method of Kaltwasser & Schlegel, "NADH-dependent coupled enzyme assay for urease and other ammonia-producing systems," *Analytical Biochemistry* 16: 132-138 (1966). The method measures the spectrophotometric change of NADH to NAD$^+$ at 340 nm in a glutamate dehydrogenase assay coupled to urease.

Cartridge Analyses Using the Improved BUN Sensor

In the preferred embodiment, the finished chips containing the sensors are then assembled into test cartridges and used to make BUN measurements in blood. One embodiment of a cartridge of the present invention is shown in FIGS. 10-13.

The cartridge is preferably adapted for insertion into a reading apparatus, and therefore has a plurality of mechanical and electrical connections for this purpose. It should also be apparent that manual operation of the cartridge is possible. Thus, after insertion of the cartridge into a reading apparatus, the reading apparatus transmits pressure onto a fluid-containing foil pack filled with approximately 130 μL of calibrant fluid located in cavity 42, rupturing the package upon spike 38, and expelling fluid into conduit 39, which is connected via a short transecting conduit in the base to the sensor conduit, 16. When the calibrant fluid contacts the sensors, they wet-up and establish an electrical signal associated with the amount of calibrating ion or molecule in the fluid.

Referring to FIG. 12, thin-film gasket 21 comprises various holes and slits to facilitate transfer of fluid between conduits within the base and the cover, and to allow the gasket to deform under pressure where necessary. Holes 30 and 33 permit one or more urea sensors and one or more reference electrode that are housed within either cutaway 35 or 37, to contact fluid within conduit 16. Referring to FIG. 13, conduit 34 is the sample holding chamber that connects the sample entry port 4 to first conduit 34 in the assembled cartridge. Cutaways 35 and 37 optionally houses a conductimetric sensor for determining the position of air-liquid boundaries. Recess 42 houses a fluid-containing package, e.g., a rupturable pouch, in the assembled cartridge that is pierced by spike 38 because of pressure exerted upon paddle 7 upon insertion into a reading apparatus. Fluid from the pierced package flows into the second conduit at 39 and then into conduit 16. An air bladder is comprised of recess 43 which is sealed on its upper surface by gasket 21. The air bladder is one embodiment of a pump means, and is actuated by pressure applied to paddle 6 which displaces air in conduit 40 and thereby displaces the sample from sample chamber 34 into conduit 16.

In the preferred embodiment, the BUN sensor is packaged into a cartridge of the type disclosed in U.S. Pat. No. 5,096,669, which also contains a calibrant solution. It is contained in a calibrant package (cal-pack), which is ruptured during the blood sample analysis. The typical sequence of events includes the cal-pack being ruptured and then the calibration solution passing over the sensor and wetting up the sensor. Typically, the cal-pack of prior art cartridges contained the following ions, sodium, potassium, calcium, chloride, bicarbonate and also HEPES buffer, glucose, lactate, urea, creatine and creatinine. As a diagnostic test for research purposes, urea was replaced with ammonia. This permits studies of the ammonium ionophore performance independent of the urease containing enzyme immobilization layer. The preferred constitution of the cal-pack for the new BUN sensor preferably include sodium, potassium, calcium, chloride, urea, HEPES buffer, glucose, lactate, creatine and creatinine.

A potentiometric chemical sensor for urea can be viewed as a system, which is constructed from functionally dissimilar components. In one embodiment of the blood urea nitrogen (BUN) sensor, the outermost layer, the one in contact with the analyte solution, permits the transport of urea while also serving to immobilize the active enzyme molecules. These enzymes catalyze the hydrolysis of urea to ammonia as described above. At neutral pH values, the ammonia thus produced exists predominantly as ammonium ions. By interposing a separate layered structure, which contains an ionophore with high sensitivity and selectivity for ammonium ions between the enzyme containing layer and a silver-silver chloride indicator electrode, the ammonium ion concentration at the electrode interface can be measured. In this type of measurement, the potential difference between the indicator electrode and a reference electrode is recorded. This is done with a potentiometric circuit in an instrument (or analyzer) which makes connection with the two electrodes, as is well known in the electrochemical measurement art. The analytical value of the measurement is derived from the fact that the magnitude of the potential difference is related by the Nicolsky equation to the concentration of the analyte, in this case, urea:

$$E=E_O+RT/nF \log [A+\Sigma(a,b)k(a,b)B]$$

where E is the measured electromotive force (signal), R is the gas law constant, T is the absolute temperature, n is the absolute value of the charge on analyte species a (e.g., n=1 for the ammonium ion), F is the Faraday constant, A is the activity of the analyte species a, B is the activity of an interfering chemical species b, k(a,b) is the interference coefficient associated with the effect of the presence of chemical species b on the electrochemical potentiometric determination of the activity of the analyte species a, and $E_0$ is a constant independent of T, A, or B. See Amman, D., *Ion-Selective Microelectrodes*, Springer, Berlin (1986) p. 68, and references cited therein, which is incorporated by reference herein.

Data presented in FIGS. 4, 5 and 15-18 were recorded and/or analyzed in using these principles. These data are presented using a commercial BUN testing system for comparison. The performance of the new sensor is superior to the established technology.

EXAMPLES

Example 1

A solution of aprotinin is prepared by dissolving 0.01 g of aprotinin in 50 mL of deionized water, generating a 0.02% concentration stock solution. An enzyme buffer solution is prepared by the addition of 4.32 g of glycerol, 130 g of deionized water, 130 g of 1M TRIS at pH 7.6, 2.6 g of 0.5M EDTA at pH 8.0, 13 g of the above 0.02% aprotinin stock solution, 0.2 g of 1,4-dithioerythritol, 2.7 g of sodium chloride, 0.097 g of potassium chloride, 0.05 g of sodium azide, 92.8 g of sucrose and 29 g of BSA. The mixture is vortexed until fully dissolved. A solution containing the acrylic resin components is then prepared, including 72.2 g of acrylamide, 150 g of deionized water, 29.4 g of 1,4-bis(acryloyl)piperazine and 2.5 g of activated carbon. This acrylic resin solution is mixed until in solution and filtered using a 0.2 um filter into a clean container. To this solution 17.8 g of 1-[4-(2-hydroxyethoxy)-phenyl]-2-hydroxy-2-methyl-1-propane-1-one is added, mixed and the solution is kept from excessive exposure to light in a container wrapped in aluminum foil. Finally 40 g of urease is added to about 333 g of the above filtered solution and mixed. About 44 g of deionized water is added, and finally 184 g of the acrylic resin solution (prepared as above) is added. The material is kept covered in aluminum foil and mixed until in solution. For long term storage, this solution is aliquoted in 1 ml portions and frozen at −60° C.

Example 2

In another embodiment of the urease enzyme immobilization layer included the enzyme carbonic anhydrase. The order of mixing is as follows: A solution of aprotinin is prepared by dissolving 0.01 g of aprotinin in 50 mL of deionized water, generating a 0.02% concentration stock solution. An enzyme buffer solution is prepared by the addition of 4.32 g of glycerol, 130 g of deionized water, 130 g of 1M Tris at pH 7.6, 2.6 g of 0.5M EDTA at pH 8.0, 13 g of the above 0.02% aprotinin stock solution, 0.2 g of 1,4-dithioerythritol, 2.7 g of sodium chloride, 0.097 g of potassium chloride, 0.05 g of sodium azide, 92.8 g of sucrose, 29 g of BSA and vortexed until the contents are fully dissolved. A solution containing the acrylic resin components is then prepared, including 72.2 g of acrylamide, 150 g of deionized water, 29.4 g of 1,4-bis(acryloyl) piperazine, and 2.5 g of activated carbon. This acrylic resin solution is mixed until in solution and filtered using a 0.2 um filter into a clean container. To this solution 17.8 g of 1-[4-(2-hydroxyethoxy)-phenyl]-2-hydroxy-2-methyl-1-propane-1-one is added, mixed and the solution is kept from excessive exposure to light using aluminum foil. Finally 40 g of urease and 14 mg of carbonic anhydrase is added to about 333 g of the above filtered enzyme solution and mixed. About 44 g of deionized water is added, and finally 184 g of the acrylic resin solution prepared above is added. The material is kept covered in aluminum foil and mixed until in solution. This solution is aliquoted in 1 ml portions and frozen at −60° C.

Any feature described or claimed with respect to any disclosed implementation may be combined in any combination with any one or more other feature(s) described or claimed with respect to any other disclosed implementation or implementations, to the extent that the features are not necessarily technically incompatible, and all such combinations are within the scope of the present invention. Furthermore, the claims appended below set forth some non-limiting combinations of features within the scope of the invention, but also contemplated as being within the scope of the invention are all possible combinations of the subject matter of any two or more of the claims, in any possible combination, provided that the combination is not necessarily technically incompatible.

The invention claimed is:

1. A sensor, comprising an electrode with a first layer covering said electrode comprising an ion-selective membrane, and a second layer covering said ion-selective membrane comprising a UV cured matrix formed from a homogeneous aqueous mixture of one or more enzymes, a humectant, an acrylic-based monomer, a water-soluble organic photo-initiator and a water-soluble acrylic-based cross-linker.

2. The sensor of claim 1, wherein said enzyme is selected from urease, glucose oxidase, lactate oxidase, creatinase, creatininase, sarcosine oxidase, catalase, carbonic anhydrase, NAD(P)H oxidase, cholesterol oxidase, alcohol oxidase, choline oxidase, glycerol-3-phosphate oxidase, thiamine oxidase, pyruvate oxidase, pyridoxal oxidase, D-amino acid oxidase, L-amino acid oxidase, alkaline phosphatase, horseradish peroxidase and combinations thereof.

3. The sensor of claim 1, wherein the monomer is selected from acrylamide, methacrylamide, N-[3-(dimethylamino)propyl]methacrylamide, hydroxyethylmethacrylate and combinations thereof.

4. The sensor of claim 1, wherein the cross-linker is selected from 1,4-bisacryloyl piperazine, N,N'(1,2-dihydroxyethylene)bis-acrylamide, N,N'-bis(acryloyl)cystamine, N,N'-methylenebisacrylamide, ethylene glycol diacrylate, (+)—N,N'-diallyltartramide and combinations thereof.

5. The sensor of claim 1, wherein the enzyme is urease and the ion-selective membrane is an ammonium ion-selective membrane.

* * * * *